US010526611B2

(12) United States Patent
Gelvin et al.

(10) Patent No.: US 10,526,611 B2
(45) Date of Patent: Jan. 7, 2020

(54) **GENE TARGETING USING MUTANT *AGROBACTERIUM* STRAINS**

(71) Applicants: Stanton B Gelvin, West Lafayette, IN (US); Lan-Ying Lee, West Lafayette, IN (US); Yaling Wang, Shanghai (CN)

(72) Inventors: Stanton B Gelvin, West Lafayette, IN (US); Lan-Ying Lee, West Lafayette, IN (US); Yaling Wang, Shanghai (CN)

(73) Assignee: Purdue Research Foundation, West Lafayette, IN (US)

( * ) Notice: Subject to any disclaimer, the term of this patent is extended or adjusted under 35 U.S.C. 154(b) by 61 days.

(21) Appl. No.: 15/301,533

(22) PCT Filed: Apr. 3, 2015

(86) PCT No.: PCT/US2015/024387
§ 371 (c)(1),
(2) Date: Oct. 3, 2016

(87) PCT Pub. No.: WO2015/154055
PCT Pub. Date: Oct. 8, 2015

(65) Prior Publication Data
US 2017/0022511 A1  Jan. 26, 2017

Related U.S. Application Data

(60) Provisional application No. 61/974,568, filed on Apr. 3, 2014.

(51) Int. Cl.
*C12N 15/82* (2006.01)
*C12N 15/87* (2006.01)

(52) U.S. Cl.
CPC ......... *C12N 15/8205* (2013.01); *C12N 15/87* (2013.01)

(58) Field of Classification Search
None
See application file for complete search history.

(56) References Cited

U.S. PATENT DOCUMENTS

2012/0297505 A1* 11/2012 Wu ...................... C07K 14/415
800/290

OTHER PUBLICATIONS

Gelvin (Traversing the cell: Agrobacterium T-DNA's journey to the host genome. Frontier in plant science, vol. 3, p. 1-11, Mar. 26, 2012).*

* cited by examiner

*Primary Examiner* — Medina A Ibrahim
*Assistant Examiner* — Wayne Zhong
(74) *Attorney, Agent, or Firm* — Purdue Research Foundation; Liang Zeng Yan

(57) ABSTRACT

The present invention provides methods and compositions for enhancing the efficiency of *Agrobacterium*-mediated transformation of host cells, such as plant cells, wherein the host cells overexpress light-dependent short hypocotyls 10 (LSH10) protein. The methods of the invention comprise *Agrobacterium*-mediated transfer of T-DNA to a plant cell, wherein the T-DNA contains a DNA of interest to be inserted into a plant genome at a homologous position.

8 Claims, 13 Drawing Sheets

Specification includes a Sequence Listing.

FIGURE 12

| Primer | Restriction site added | Sequence[a] | Target vector[b] | Vector cloning site | Purpose |
|---|---|---|---|---|---|
| GALLS-F | BamHI | TTGGATCCGCATGCCAACCGACGAC | Peg202 | BamHI | Bait for Y2H |
| GALLS-R | XhoI | TTCTCGAGTTAGAGTCCACGTCC | Peg202 | XhoI | Bait for Y2H |
| GIP-ADS | NdeI | AGCTCATATGTCCTCTCCAAGAGAAAGAG | Pgadt7, Pgad424 | NdeI | Prey for Y2H |
| GIP-ADA | BamHI | CGTAGGATCCAGTCTTTCACGACGATGGAG | Pgadt7, Pgad424 | BamHI | Prey for Y2H |
| GIP-OE-F | XhoI | GCAACTCGAGCGAGCTTACACTCAACAAG AG | E1774 | XhoI | Overexpression |
| GIP-OE-R | SpeI | CACTACTAGTGACATAGAAGTACGCTGATC C | E1774 | SpeI | Overexpression |
| GST-GIPF | BamHI | GGATCCTCATGTCCTCTCCAAGAGAAAG | Pgex5X-1 | BamHI | GST pull-down |
| GST-GIPR | EcoRI | GAATTCAGTCTTTCACGACGATGGAG | Pgex5X-1 | EcoRI | GST pull-down |
| LSH10/GIP-S | BglII | AAATAGATCTCGATGTCCTCTCCAAGAG | E3308 (Psat1-GIP-nVenus) | BglII | BiFC, subcellular localization |
| LSH10/GIP-R | BamHI | ATTTGGATCCAGAGAAGCTGAAGGAAG | E3308 (Psat1-GIP-nVenus) | BamHI | BiFC, subcellular localization |
| LSH10-10p-S | AgeI | GACAACCGGTGAAAACGGCCATAAAATGAC GAT | E3185 | AgeI | Native promoter |
| LSH10-10p-R | BamHI | GTGAGGATCCGTGCTCTGATCCTGATGAT TC | E3185 | BamHI | Native promoter |
| gallex 3 | BglII | CATGGCACATCACCATCACCATCACACCGA CGACATTGTAATGTCCGATCCGGAATGGC TGCTGTTGACACGTCGTCTGTCCCTATGCGCTTC CAGACAGATCTGCTAC | pTrc99 | NcoI | 6-His tag GALLS |
| gallex 4 | BglII | CAGATCTGTCTGGAAGCGCATAGGGACAGA CGTGTCAACAGCAGCCATTCCGGGATCGGA CATTACAATGTCGTCGGTGTGATGGTGATG GTGATGTGC | pTrc99 | KpnI | 6-His tag GALLS |
| gallex 5 | SacII | CGCGGGGGATGGAGACGTGGACTCTAAG | Plh378 | BamHI-KpnI | GALLS C-terminus |
| gallex 6 | SacII | GATCCTTAGAGTCCACGTCCATCCCCGCGG TAC | Plh378 | BamHI-KpnI | GALLS C-terminus |
| ESBFwd | EcoRI | AATTCTAAATAGTGAG | Plh388 | EcoRI-BamHI | In-frame stop in GALLS |

FIGURE 12 (cont'd)

| | EcoRI | GATCCTCACTATTAG | pLH388 | EcoRI-BamHI | In-frame stop in GALLS |
|---|---|---|---|---|---|
| ESBRev | | | | | |
| strep F | none | CATGGCATGGAGCCACCGCAGTTCGAAAAGCG | pLH451 | NcoI | Strep-6-His tag GALLS |
| strep R | none | CATGCGCTTTTCGAACTGCGGGTGGCTCCA | pLH451 | NcoI | Strep-6-His tag GALLS |
| Δ7-23-nVenus-U | SalI | GTCCAGTGACTCTTCTCTGGAGAGGACATG | E3308 | SalI | BiFC, subcellular localization |
| Δ7-23-nVenus-L | SalI | GATGCGTCGACAGCCGTTACGAGTCGCAGAA | E3308 | SalI | BiFC, subcellular localization |
| Δ22-71-nVenus-U | SalI | CACTAGTCGACGTCACCGGTGGCTCTGAT | E3308 | SalI | BiFC, subcellular localization |
| Δ22-71-nVenus-L | SalI | GTGTAGTCGACCTGTATGTTCTACGGCCAG | E3308 | SalI | BiFC, subcellular localization |
| Δ77-144-nVenus-U | SalI | CATGAGTCGACAGGCACGTGCACCTTTGT | E3308 | SalI | BiFC, subcellular localization |
| Δ77-144-nVenus-L | SalI | GACGAGTCGACGGGATTCCTACAAGAAGAAGAAG | E3308 | SalI | BiFC, subcellular localization |
| Δ57-119-nVenus-U | SalI | GTCTGTCGACGTTACAGCTGCAGTGAGACATC | E3308 | SalI | BiFC, subcellular localization |
| Δ57-119-nVenus-L | SalI | GACTGTCGACGAGAGTAACCCTTTCGCTAGC | E3308 | SalI | BiFC, subcellular localization |
| Δ149-155-nVenus-U | SalI | GACTGTCGACGTAAGGAATCCCTCTAGCCTTAGC | E3308 | SalI | BiFC, subcellular localization |
| Δ149-155-nVenus-L | SalI | GACTGTCGACCCAACGCCGGAGATGGGA | E3308 | SalI | BiFC, subcellular localization |
| Δ152-177-nVenus-U | NcoI | CGTACCATGGTCATGTCCTCTCCAAGAGAAAG | E3308 | NcoI | BiFC, subcellular localization |
| Δ152-177-nVenus-R | SalI | GTACGTCGACTCTTCTTCTTGTAAGGAATCCCTC | E3308 | SalI | BiFC, subcellular localization |
| GIP-RTF | --- | AGATGGGAGGTGGGAGAGAG | --- | --- | RT-PCR |
| GIP-RTR | --- | ATCTGCGGAAATGAAGAGGA | --- | --- | RT-PCR |
| ACT2-F | --- | CTTGCACCAAGCAGCATGAA | --- | --- | RT-PCR |
| ACT2-R | --- | CCGATCCAGACACTGTACTTCCTT | --- | --- | RT-PCR |

[a] Restriction endonuclease sites are underlined.
[b] E indicates Gelvin laboratory stock number.

SEQUENCE LISTING

<160> NUMBER OF SEQ ID NOS: 38

<210> SEQ ID NO 1

<211> LENGTH: 25
<212> TYPE: DNA
<213> ORGANISM: Unknown
<220> FEATURE:
<223> OTHER INFORMATION: Primer

<400> SEQUENCE: 1
ttggatccgc atgccaaccg acgac                                           25

<210> SEQ ID NO 2
<211> LENGTH: 23
<212> TYPE: DNA
<213> ORGANISM: Unknown
<220> FEATURE:
<223> OTHER INFORMATION: Primer

<400> SEQUENCE: 2
ttctcgagtt agagtccacg tcc                                             23

<210> SEQ ID NO 3
<211> LENGTH: 29
<212> TYPE: DNA
<213> ORGANISM: Unknown
<220> FEATURE:
<223> OTHER INFORMATION: Primer

<400> SEQUENCE: 3
agctcatatg tcctctccaa gagaaagag                                       29

<210> SEQ ID NO 4
<211> LENGTH: 30
<212> TYPE: DNA
<213> ORGANISM: Unknown
<220> FEATURE:
<223> OTHER INFORMATION: Primer

<400> SEQUENCE: 4
cgtaggatcc agtctttcac gacgatggag                                      30

<210> SEQ ID NO 5
<211> LENGTH: 31
<212> TYPE: DNA
<213> ORGANISM: Unknown
<220> FEATURE:
<223> OTHER INFORMATION: Primer

<400> SEQUENCE: 5
gcaactcgag cgagcttaca ctcaacaaga g                                    31

<210> SEQ ID NO 6
<211> LENGTH: 31
<212> TYPE: DNA
<213> ORGANISM: Unknown
<220> FEATURE:
<223> OTHER INFORMATION: Primer

<400> SEQUENCE: 6
cactactagt gacatagaag tacgctgatc c                                    31

<210> SEQ ID NO 7
<211> LENGTH: 28
<212> TYPE: DNA
<213> ORGANISM: Unknown
<220> FEATURE:
<223> OTHER INFORMATION: Primer

<400> SEQUENCE: 7
ggatcctcat gtcctctcca agagaaag                                        28

<210> SEQ ID NO 8
<211> LENGTH: 26
<212> TYPE: DNA
<213> ORGANISM: Unknown
<220> FEATURE:
<223> OTHER INFORMATION: Primer

<400> SEQUENCE: 8
gaattcagtc tttcacgacg atggag                                          26

<210> SEQ ID NO 9
<211> LENGTH: 28
<212> TYPE: DNA
<213> ORGANISM: Unknown
<220> FEATURE:
<223> OTHER INFORMATION: Primer

<400> SEQUENCE: 9
aaatagatct cgatgtcctc tccaagag                                        28

<210> SEQ ID NO 10
<211> LENGTH: 28
<212> TYPE: DNA
<213> ORGANISM: Unknown
<220> FEATURE:
<223> OTHER INFORMATION: Primer

<400> SEQUENCE: 10
atttggatcc cagagaagct gaaggaag                                        28

<210> SEQ ID NO 11
<211> LENGTH: 32
<212> TYPE: DNA
<213> ORGANISM: Unknown
<220> FEATURE:
<223> OTHER INFORMATION: Primer

<400> SEQUENCE: 11
gacaaccggt gaaacggcca taaaatgacg at                                   32

<210> SEQ ID NO 12
<211> LENGTH: 32
<212> TYPE: DNA
<213> ORGANISM: Unknown
<220> FEATURE:
<223> OTHER INFORMATION: Primer

<400> SEQUENCE: 12
gtgaggatcc gtggctctga tcctgatgat tc                                   32

<210> SEQ ID NO 13
<211> LENGTH: 107
<212> TYPE: DNA
<213> ORGANISM: Unknown
<220> FEATURE:
<223> OTHER INFORMATION: Primer

<400> SEQUENCE: 13
catggcacat caccatcacc atcacaccga cgacattgta atgtccgatc ccggaatggc     60
tgctgttgac acgtctgtcc ctatgcgctt ccagacagat ctggtac                  107

<210> SEQ ID NO 14

```
<211> LENGTH: 99
<212> TYPE: DNA
<213> ORGANISM: Unknown
<220> FEATURE:
<223> OTHER INFORMATION: Primer

<400> SEQUENCE: 14
cagatctgtc tggaagcgca tagggacaga cgtgtcaaca gcagccattc cgggatcgga      60
cattacaatg tcgtcggtgt gatggtgatg gtgatgtgc                             99

<210> SEQ ID NO 15
<211> LENGTH: 25
<212> TYPE: DNA
<213> ORGANISM: Unknown
<220> FEATURE:
<223> OTHER INFORMATION: Primer

<400> SEQUENCE: 15
cgcggggatg gacgtggact ctaag                                            25

<210> SEQ ID NO 16
<211> LENGTH: 33
<212> TYPE: DNA
<213> ORGANISM: Unknown
<220> FEATURE:
<223> OTHER INFORMATION: Primer

<400> SEQUENCE: 16
gatccttaga gtccacgtcc atccccgcgg tac                                   33

<210> SEQ ID NO 17
<211> LENGTH: 15
<212> TYPE: DNA
<213> ORGANISM: Unknown
<220> FEATURE:
<223> OTHER INFORMATION: Primer

<400> SEQUENCE: 17
aattctaata gtgag                                                       15

<210> SEQ ID NO 18
<211> LENGTH: 15
<212> TYPE: DNA
<213> ORGANISM: Unknown
<220> FEATURE:
<223> OTHER INFORMATION: Primer

<400> SEQUENCE: 18
gatcctcact attag                                                       15

<210> SEQ ID NO 19
<211> LENGTH: 33
<212> TYPE: DNA
<213> ORGANISM: Unknown
<220> FEATURE:
<223> OTHER INFORMATION: Primer

<400> SEQUENCE: 19
catggcatgg agccacccgc agttcgaaaa gcg                                   33

<210> SEQ ID NO 20
<211> LENGTH: 30
<212> TYPE: DNA
<213> ORGANISM: Unknown
<220> FEATURE:
<223> OTHER INFORMATION: Primer
```

<400> SEQUENCE: 20
catgcgcttt tcgaactgcg ggtggctcca    30

<210> SEQ ID NO 21
<211> LENGTH: 33
<212> TYPE: DNA
<213> ORGANISM: Unknown
<220> FEATURE:
<223> OTHER INFORMATION: Primer

<400> SEQUENCE: 21
gtccagtcga ctctttctct tggagaggac atg    33

<210> SEQ ID NO 22
<211> LENGTH: 31
<212> TYPE: DNA
<213> ORGANISM: Unknown
<220> FEATURE:
<223> OTHER INFORMATION: Primer

<400> SEQUENCE: 22
gatgcgtcga cagccgttac gagtcgcaga a    31

<210> SEQ ID NO 23
<211> LENGTH: 29
<212> TYPE: DNA
<213> ORGANISM: Unknown
<220> FEATURE:
<223> OTHER INFORMATION: Primer

<400> SEQUENCE: 23
cactagtcga cgtcaccggt ggctctgat    29

<210> SEQ ID NO 24
<211> LENGTH: 30
<212> TYPE: DNA
<213> ORGANISM: Unknown
<220> FEATURE:
<223> OTHER INFORMATION: Primer

<400> SEQUENCE: 24
gtgtagtcga cctgtatgtt ctacggccag    30

<210> SEQ ID NO 25
<211> LENGTH: 29
<212> TYPE: DNA
<213> ORGANISM: Unknown
<220> FEATURE:
<223> OTHER INFORMATION: Primer

<400> SEQUENCE: 25
catgagtcga caggcacgtg cacctttgt    29

<210> SEQ ID NO 26
<211> LENGTH: 35
<212> TYPE: DNA
<213> ORGANISM: Unknown
<220> FEATURE:
<223> OTHER INFORMATION: Primer

<400> SEQUENCE: 26
gacgagtcga cgggattcct tacaagaaga agaag    35

<210> SEQ ID NO 27

-continued

```
<211> LENGTH: 32
<212> TYPE: DNA
<213> ORGANISM: Unknown
<220> FEATURE:
<223> OTHER INFORMATION: Primer

<400> SEQUENCE: 27
gtctgtcgac gttacagctg cagtgagaca tc                                32

<210> SEQ ID NO 28
<211> LENGTH: 31
<212> TYPE: DNA
<213> ORGANISM: Unknown
<220> FEATURE:
<223> OTHER INFORMATION: Primer

<400> SEQUENCE: 28
gactgtcgac gagactaacc ctttcgctag c                                 31

<210> SEQ ID NO 29
<211> LENGTH: 34
<212> TYPE: DNA
<213> ORGANISM: Unknown
<220> FEATURE:
<223> OTHER INFORMATION: Primer

<400> SEQUENCE: 29
gactgtcgac gtaaggaatc cctctagcct tagc                              34

<210> SEQ ID NO 30
<211> LENGTH: 28
<212> TYPE: DNA
<213> ORGANISM: Unknown
<220> FEATURE:
<223> OTHER INFORMATION: Primer

<400> SEQUENCE: 30
gactgtcgac ccaacgccgg agatggga                                     28

<210> SEQ ID NO 31
<211> LENGTH: 32
<212> TYPE: DNA
<213> ORGANISM: Unknown
<220> FEATURE:
<223> OTHER INFORMATION: Primer

<400> SEQUENCE: 31
cgtaccatgg tcatgtcctc tccaagagaa ag                                32

<210> SEQ ID NO 32
<211> LENGTH: 34
<212> TYPE: DNA
<213> ORGANISM: Unknown
<220> FEATURE:
<223> OTHER INFORMATION: Primer

<400> SEQUENCE: 32
gtacgtcgac tcttcttctt gtaaggaatc cctc                              34

<210> SEQ ID NO 33
<211> LENGTH: 20
<212> TYPE: DNA
<213> ORGANISM: Unknown
<220> FEATURE:
<223> OTHER INFORMATION: Primer

<400> SEQUENCE: 33
```

```
agatgggagg tgggagagag                                              20

<210> SEQ ID NO 34
<211> LENGTH: 20
<212> TYPE: DNA
<213> ORGANISM: Unknown
<220> FEATURE:
<223> OTHER INFORMATION: Primer

<400> SEQUENCE: 34
atctgcggaa atgaagagga                                              20

<210> SEQ ID NO 35
<211> LENGTH: 20
<212> TYPE: DNA
<213> ORGANISM: Unknown
<220> FEATURE:
<223> OTHER INFORMATION: Primer

<400> SEQUENCE: 35
cttgcaccaa gcagcatgaa                                              20

<210> SEQ ID NO 36
<211> LENGTH: 24
<212> TYPE: DNA
<213> ORGANISM: Unknown
<220> FEATURE:
<223> OTHER INFORMATION: Primer

<400> SEQUENCE: 36
ccgatccaga cactgtactt cctt                                         24

<210> SEQ ID NO 37
<211> LENGTH: 177
<212> TYPE: PRT
<213> ORGANISM: Arabidopsis thaliana

<400> SEQUENCE: 37

Met Ser Ser Pro Arg Glu Arg Gly Lys Ser Leu Met Glu Ser Ser Gly
1               5                   10                  15

Ser Glu Pro Pro Val Thr Pro Ser Arg Tyr Glu Ser Gln Lys Arg Arg
            20                  25                  30

Asp Trp Asn Thr Phe Gly Gln Tyr Leu Lys Asn Gln Arg Pro Pro Val
        35                  40                  45

Pro Met Ser His Cys Ser Cys Asn His Val Leu Asp Phe Leu Arg Tyr
    50                  55                  60

Leu Asp Gln Phe Gly Lys Thr Lys Val His Val Pro Gly Cys Met Phe
65                  70                  75                  80

Tyr Gly Gln Pro Glu Pro Pro Ala Pro Cys Thr Cys Pro Leu Arg Gln
                85                  90                  95

Ala Trp Gly Ser Leu Asp Ala Leu Ile Gly Arg Leu Arg Ala Ala Tyr
            100                 105                 110

Glu Glu Asn Gly Gly Pro Pro Glu Thr Asn Pro Phe Ala Ser Gly Ala
        115                 120                 125

Ile Arg Val Tyr Leu Arg Glu Val Arg Glu Cys Gln Ala Lys Ala Arg
    130                 135                 140

Gly Ile Pro Tyr Lys Lys Lys Lys Lys Lys Pro Thr Pro Glu Met
145                 150                 155                 160

Gly Gly Gly Arg Glu Asp Ser Ser Ser Ser Ser Ser Phe Ser Phe
                165                 170                 175
```

```
Ser

<210> SEQ ID NO 38
<211> LENGTH: 127
<212> TYPE: PRT
<213> ORGANISM: Arabidopsis thaliana

<400> SEQUENCE: 38

Pro Ser Arg Tyr Glu Ser Gln Lys Arg Arg Asp Trp Asn Thr Phe Gly
1               5                   10                  15

Gln Tyr Leu Lys Asn Gln Arg Pro Pro Val Pro Met Ser His Cys Ser
            20                  25                  30

Cys Asn His Val Leu Asp Phe Leu Arg Tyr Leu Asp Gln Phe Gly Lys
            35                  40                  45

Thr Lys Val His Val Pro Gly Cys Met Phe Tyr Gly Gln Pro Glu Pro
        50                  55                  60

Pro Ala Pro Cys Thr Cys Pro Leu Arg Gln Ala Trp Gly Ser Leu Asp
65                  70                  75                  80

Ala Leu Ile Gly Arg Leu Arg Ala Ala Tyr Glu Glu Asn Gly Gly Pro
                85                  90                  95

Pro Glu Thr Asn Pro Phe Ala Ser Gly Ala Ile Arg Val Tyr Leu Arg
            100                 105                 110

Glu Val Arg Glu Cys Gln Ala Lys Ala Arg Gly Ile Pro Tyr Lys
            115                 120                 125
```

GENE TARGETING USING MUTANT *AGROBACTERIUM* STRAINS

The present application is a national stage entry under 35 U.S.C. § 371(b) of International Application No. PCT/US2015/024387, filed on Apr. 3, 2015, which claims priority under 35 U.S.C. § 119(e) to U.S. Provisional Application Ser. No. 61/974,568, filed on Apr. 3, 2014, which is hereby incorporated by reference in its entirety.

This invention was made with government support under MCB-1049836 awarded by the National Science Foundation. The government has certain rights in the invention.

TECHNICAL FIELD

The present disclosure generally relates to plant transformation using mutant *Agrobacterium* strains, and in particular to a method of site directed homologous recombination using transgenic plants and mutant *Agrobacterium*.

BACKGROUND

This section introduces aspects that may help facilitate a better understanding of the disclosure. Accordingly, these statements are to be read in this light and are not to be understood as admissions about what is or is not prior art.

*Agrobacterium* harboring a Ti or a Ri plasmid can efficiently transfer a portion of these plasmids, the T-DNA, into plant cells. Transfer of the T-DNA into the plant cell is induced by signal compounds present at the site of a plant wound and requires T-DNA border sequences at both ends of the T-DNA and trans-acting virulence gene products (vir) encoded by the Ti or Ri plasmid. The transferred T-DNA is then targeted to the nucleus and integrated into the plant genome.

Light-dependent short hypocotyls (LSH) proteins found in plants are known to mediate light regulation in seedling development, meristem maintenance, and shoot regeneration. There are currently ten known family members of this protein family, and structurally they contain a central domain of unknown function (DUF640) flanked by amino- and carboxy-terminal variable domains. LSH proteins also contain putative monopartite SV40-type NLS sequences overlapping the DUF640 and the adjacent carboxy-terminal variable domain.

A number of techniques exist for introducing exogenous DNA into plant cells, such as protoplasts, which are capable of subsequent regeneration, such as, microinjection of naked DNA, electroporation, Ca/PEG precipitation, and particle bombardment-mediated delivery, so called "biolistics."

A common previously utilized technique for the genetic engineering of plants involves the use of the soil-dwelling plant pathogenic bacterium *Agrobacterium*. *Agrobacterium* has the natural ability to transfer a portion of its DNA, referred to as T-DNA, into the genome of susceptible plant cells. By changing the native T-DNA in an *Agrobacterium* strain, it is possible to use this unique trait of *Agrobacterium* to transfer desired genes into single plant cells. While *Agrobacterium* are typically restricted to infecting dicotyledonous species under natural conditions, by manipulating the conditions of infection, efficient transformation of monocots, including some crop species has been possible. Common to the methods specified above is the integration of the exogenous DNA into a random site in the plant chromosome. While useful for many applications, random integration of transgenes leaves a number of difficulties. For example, the targeted disruption of an endogenous gene requires that integration occur at a specified locus in the host plant genome. Gene targeting is difficult when using the *Agrobacterium* method of transformation, because an *Agrobacterium* protein called VirE2 masks the naked T-DNA when transfected into the host plant cell, which blocks any chance of site directed genetic modification by homologous recombination.

Currently, there is not an elegant solution to transform cells with T-DNA at a site of interest in the host genome.

SUMMARY OF THE INVENTION

In one aspect of the present invention there is provided a transgenic plant or part thereof transformed with a polynucleotide sequence encoding a LSH10 polypeptide (SEQ ID NO: 37), operably linked to a heterologous promoter functional in the plant or part thereof, wherein the plant or part thereof may exhibit increased transformability by *Agrobacterium*-mediated transformation relative to a plant or part thereof lacking the polynucleotide sequence. The LSH10 polypeptide encoded by a nucleic acid sequence may be substantially the entire LSH10 polypeptide or alternatively, the LSH10 polypeptide encoded by a nucleic acid sequence may be a truncated polypeptide comprising the conserved DUF640 domain (SEQ ID NO: 38). The transgenic plant of the present invention may be a dicot or it may be a monocot.

Overexpression of the LSH10 polypeptide above basal levels increases the levels of *Agrobacterium*-mediated transformation. In another aspect, the transgenic plant of the present invention exhibits increased transformability by *Agrobacterium*-mediated transformation wherein the *Agrobacterium* strains may comprise GALLS or VirE2, proteins that have been shown to mediate transformation. Alternatively, the *Agrobacterium* strains may lack both GALLS and VirE2.

In a further embodiment of the present invention, methods are provided for increased transformability of a plant or plant cell by *Agrobacterium*-mediated transformation comprising overexpressing a LSH10 polypeptide in the plant or plant cell. The amount of LSH10 expression may be from about 2 to about 10 times greater than basal level.

In yet another aspect of the present invention, there are provided methods of transformation comprising: a) expressing a transgenic polynucleotide sequence encoding a LSH10 polypeptide in a plant cell susceptible to *Agrobacterium*-mediated transformation; and b) transforming the plant cell with a selected DNA by *Agrobacterium*-mediated transformation; wherein the efficiency of transformation is increased relative to a cell of the same genotype not expressing the transgenic sequence.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

FIG. 12 is a chart with a listing of example primers included herein, wherein GALLS-F is assigned SEQ ID NO: 1; GALLS-R is assigned SEQ ID NO: 2; GIP-ADS is assigned SEQ ID NO: 3; GIP-ADA is assigned SEQ ID NO: 4; GIP-OE-F is assigned SEQ ID NO: 5; GIP-OE-R is assigned SEQ ID NO: 6; GST-GIPF is assigned SEQ ID NO: 7; GST-GIPR is assigned SEQ ID NO: 8; LSH10/GIP-S is assigned SEQ ID NO: 9; LSH10/GIP-R is assigned SEQ ID NO: 10; LSH10-10p-S is assigned SEQ ID NO: 11; LSH10-10p-R is assigned SEQ ID NO: 12; gallex 3 is assigned SEQ ID NO: 13; gallex 4 is assigned SEQ ID NO: 14; gallex 5 is assigned SEQ ID NO: 15; gallex 6 is assigned SEQ ID NO: 16; ESBFwd is assigned SEQ ID NO: 17; ESBRev is assigned SEQ ID NO: 18; strep F is assigned SEQ ID NO: 19; strep R is assigned SEQ ID NO: 20; Δ7-23-nVenus-U is assigned SEQ ID NO: 21; Δ7-23-nVenus-L is assigned SEQ ID NO: 22; Δ22-71-nVenus-U is assigned SEQ ID NO: 23; Δ22-71-nVenus-L is assigned SEQ ID NO: 24; Δ77-144-nVenus-U is assigned SEQ ID NO: 25; Δ77-144-nVenus-L is assigned SEQ ID NO: 26; Δ57-119-nVenus-U is assigned SEQ ID NO: 27; Δ57-119-nVenus-L is assigned SEQ ID NO: 28; Δ149-155-nVenus-U is assigned SEQ ID NO: 29; Δ149-155-nVenus-L is assigned SEQ ID NO: 30; Δ152-177-nVenus-S is assigned SEQ ID NO: 31; Δ152-177-nVenus-R is assigned SEQ ID NO: 32; GIP-RTF is assigned SEQ ID NO: 33; GIP-RTR is assigned SEQ ID NO: 34; ACT2-F is assigned SEQ ID NO: 35; ACT2-R is assigned SEQ ID NO: 36.

DETAILED DESCRIPTION

Figure 1A:
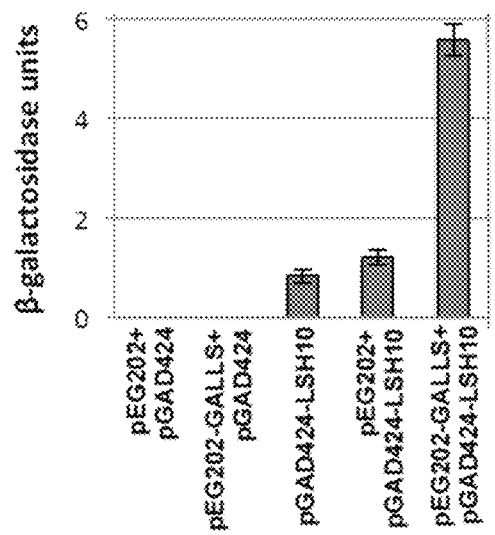
FIG. 1A is a graph showing the interaction of LSH10 with GALLS-FL in yeast.

In one aspect of the present invention there is provided a transgenic plant or part thereof transformed with a polynucleotide sequence encoding a LSH10 polypeptide, operably linked to a heterologous promoter functional in the plant or part thereof, wherein the plant or part thereof may exhibit increased transformability by *Agrobacterium*-mediated transformation relative to a plant or part thereof lacking the polynucleotide sequence. The LSH10 polypeptide encoded by a nucleic acid sequence may be substantially the entire LSH10 polypeptide or alternatively, the LSH10 polypeptide encoded by a nucleic acid sequence may be a truncated polypeptide comprising the conserved DUF640 domain. The transgenic plant of the present invention may be a dicot or it may be a monocot.

Overexpression of the LSH10 polypeptide above basal levels increases the levels of *Agrobacterium*-mediated transformation. In another embodiment, the transgenic plant of the present invention exhibits increased transformability by *Agrobacterium*-mediated transformation wherein the *Agrobacterium* strains may comprise GALLS or VirE2, proteins that have been shown to mediate transformation. Alternatively, the *Agrobacterium* strains may lack both GALLS and VirE2. Overexpression of LSH10 allows for reliable *Agrobacterium*-mediated transformation in the presence and absence of proteins such as GALLS and VirE2, which have been shown to mediate transformation. Thus the present invention may allow for the use of additional *Agrobacterium* strains and mutants than are presently used in the art.

In one aspect, the invention provides a transgenic plant or part thereof transformed with a polynucleotide sequence that encodes a LSH10 polypeptide or LSH10-like polypeptide, operably linked to a heterologous promoter. The promoter operably linked to the gene encoding the LSH10 polypeptide or LSH10-like polypeptide may be a promoter functional in a plant cell. In certain embodiments, the LSH10 polypeptide may be encoded by a nucleic acid sequence comprising the entire coding region for LSH10. The nucleic acid sequence may be, but not limited to, GenBank Accession Nos. AK118714.1 or AF218765.1. Alternatively, the LSH10 polypeptide may be a truncated polypeptide, comprising the conserved DUF640 domain (FIG. 9) which is from approximately amino acid position 23 to amino acid 149-155. It will be appreciated that the DUF640 region may be larger or smaller than the example given here.

In another aspect, the present invention also may include those polypeptides which exhibit at least 85%, more preferably at least 90% identity, and most preferably at least 95% identity to a polypeptide sequence selected from the group of sequences set forth above. "Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. Computer programs can be used to determine "identity" between two sequences these programs include but are not limited to, GCG; suite of five BLAST programs, three designed for nucleotide sequences queries (BLASTN, BLASTX, and TBLASTX) and two designed for protein sequence queries (BLASTP and TBLASTN). The BLAST X program is publicly available from NCBI and other sources. The well-known Smith Waterman algorithm can also be used to determine identity.

The invention therefore provides nucleic acids encoding polypeptide described herein. The nucleic acid may be defined as comprising nucleic acids encoding, in frame, the polypeptide. Those of skill in the art will understand in view of the disclosure that such nucleic acids may be provided as an expression construct by linking appropriate regulatory elements to the nucleic acid corresponding to a host cell in which heterologous expression is desired. For plant expression, a plant promoter may be operably linked to the nucleic acid. In addition, other elements such as enhancers, terminators and transit peptides may be used. Endogenous or heterologous elements may be used. For example, MtIOMT could be placed at the N-terminus of the encoded polypeptide in order to utilize a native endoplasmic reticulum localization peptide.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with coding sequences that alter plant secondary metabolite biosynthesis as described herein. The coding sequences may be provided with other sequences such as regulatory elements or other coding sequences. Where a selectable or screenable marker is used, one may employ the separate coding regions on either the same or different DNA segments for transformation. In the latter case, the different vectors are delivered concurrently to recipient cells to maximize co-transformation.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes.

Particularly useful for transformation are expression cassettes which have been isolated from such vectors. DNA segments used for transforming plant cells will, of course, generally comprise coding sequence which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components that may be included with plant transformation vectors are as follows.

In certain embodiments, the invention also provides a cell or seed of the transgenic plant, or of a subsequent generation of the transgenic plant, wherein the cell or seed comprise the LSH10 or LSH10-like polypeptide, or the polynucleotide sequence encoding the LSH10 or LSH10-like polypeptide.

In another aspect, the invention provides a method of enhancing the efficiency of Agrobacterium-mediated transformation of a host cell, comprising expressing in the cell a heterologous polynucleotide encoding LSH10, operably linked to a heterologous promoter functional in a plant cell. In the method, the host cell may be transformed with an Agrobacterium transformation vector comprising a T-DNA sequence simultaneously with the LSH10 or LSH10-like encoding sequence or following transformation of the host cell with a LSH10 or LSH10-like coding sequence. For example, the transforming may be carried within any time period in which an increase in transformation efficiency is observed. In certain embodiments the host cell is stably transformed with the polynucleotide sequence.

In specific embodiments, the host cell is defined as expressing the LSH10 polypeptide at the time the host cell is transformed by Agrobacterium-meditated transformation. In the method, the host cell may be a plant cell and may be a dicot or monocot plant cell. Non-limiting examples of dicots include cotton, soybean, rapeseed, sunflower, tobacco, sugarbeet, or alfalfa. Non-limiting examples of monocots include corn, rice, wheat, sorghum, barley, oat, and turfgrass. The host cell may also be, for example, a fungal cell.

In still another aspect, the invention provides a method of transformation comprising a) providing a cell prepared by a method of the invention to express heterologous LSH10; and b) transforming the cell with a selected DNA by Agrobacterium-mediated transformation, wherein the efficiency of transformation is increased relative to a cell not expressing a transgenic sequence encoding LSH10 function. In the method, the host cell may be a plant cell and may be a dicot or monocot plant cell. Non-limiting examples of dicots include cotton, soybean, rapeseed, sunflower, tobacco, sugarbeet, or alfalfa. Non-limiting examples of monocots include corn, rice, wheat, sorghum, barley, oat, and turfgrass. The host cell may also be, for example, a fungal cell In certain embodiments a plant sample is transgenically modified to overexpress LSH proteins at above the basal expression level. By "above basal expression level" is meant that the proteins are upregulated or expressed in higher amounts or more often than compared to wild-type or basal level of expression in wild type plant cells. In certain embodiments the preferred LSH protein overexpressed is LSH10.

In certain embodiments an *Agrobacterium* comprises a mutation in the virE2 gene, so that the VirE2 protein is not expressed, a functional VirE2 protein is not expressed, or an alternative protein that is not the wild-type version of VirE2 is expressed. In certain embodiments the type of *Agrobacterium* used in the process of transfecting a plant sample with T-DNA does not naturally express VirE2 protein.

In certain embodiments an *Agrobacterium* comprises a mutation in the GALLS gene, so that the GALLS protein is not expressed, a functional GALLS protein is not expressed, or an alternative protein that is not the wild-type version of GALLS is expressed. In certain embodiments the type of *Agrobacterium* used in the process of transfecting a plant sample with T-DNA does not naturally express GALLS protein.

In certain embodiments a portion of the T-DNA comprises a DNA or RNA of interest designed to knock-out a gene of interest in the at least one plant cell. In certain embodiments a portion of the T-DNA is designed to knock-in a gene of interest in the at least one plant cell. In certain embodiments a portion of the T-DNA is designed to alter the basal level of expression of at least one protein in the at least one plant cell.

In one embodiment the method includes a T-DNA with a percent homology to the plant sample genome that it allows for recombining and homologous recombination.

In one embodiment the method may include *Agrobacterium*-mediated transfer of T-DNA to a plant cell, wherein the T-DNA includes a DNA of interest flanked by target sites for a site-specific recombinase. In certain embodiments the DNA of interest on the T-DNA has 0-100 percent homology with any sequence in the plant sample genome, and the flanking sequences have between 20-100 percent homology to help direct homologous recombination. In certain embodiments the flanking sequences are directly repeated target sites for site-specific homologous recombinase. The DNA of interest may also contain a non-identical target site for the recombinase. An expression cassette for the site-specific recombinase is present on the T-DNA or the plant genome, or is transiently introduced into the plant cell.

Plants cells stably transformed with a site-specific recombinase expression cassette can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of plant Cell Culture*, MacMillan Publishing Company, New York, pp. 124-176 (1983); and Binding, *Regeneration of Plants, Plant Protoplasts*, CRC Press, Boca Raton, pp. 21-73 (1985).

Techniques for transforming a wide variety of higher plant species are well known and described in the technical, scientific, and patent literature. See, for example, Weising et al. *Ann. Rev. Genet.* 22: 421-477 (1988). In preferred embodiments, the T-DNA is transferred into the transgenically modified plant expressing LSH proteins above basal level, without the assistance of any scaffold or delivery devices outside of the machinery within the plant cell.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

References and citations to other documents, such as patents, patent applications, patent publications, journals, books, papers, web contents, have been made throughout this disclosure. All such documents are hereby incorporated herein by reference in their entirety for all purposes.

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The following examples are provided as a means of illustration and not as a means of limitation.

EXAMPLES

Methods:

Plant and Bacterial Material and Growth Conditions:

*Arabidopsis thaliana* plants were grown in a mixture of vermiculite, perlite, and peat moss (1:1:1) in an environmental chamber with a long photoperiod (16 h light/8 h dark) at 22° C. For axenic growth, seeds were surface sterilized with 50% bleach and 0.1% sodium dodecylsulfate and plated on Gamborg's B5 medium (Caisson Laboratories, Logan, Utah) agar plates containing 2% sucrose, 100 µg/ml timentin (GlaxoSmithKline), and (when appropriate) selective antibiotics (µg/ml: kanamycin, 50; hygromycin, 20; phosphinothricin [Duchefa, Haarlem, The Netherlands], 10). After 1-2 d of stratification at 4° C., the plates were maintained at 16 h light (100 µmol·m-2·s-120)/8 h dark at 22° C. Tobacco (*Nicotiana tabacum*) Bright Yellow (BY)-2 cells were maintained as previously described (Tenea et al., (2009) Plant Cell 21:3350-3367). T-DNA insertion lines were obtained from the *Arabidopsis* Biological Resource Center (www.arabidopsis.org). *Agrobacterium* strains were grown in YEP or AB minimal media (Lichtenstein and Draper, (1986) In DM Glover ed, Genetic Engineering of Plants, Vol 2. IRL Press, Washington, D.C. pp 67-119) with the appropriate antibiotics.

Yeast Two-Hybrid Assays:

To screen for *Arabidopsis* GALLS-interacting proteins, we fused the full-length GALLS (GALLS-FL) gene in frame with lexA in the yeast bait expression vector pEG202 (Fields and Song, (1989) Nature 340: 245-246). Using primers listed in FIG. 12 and PfuTurbo DNA polymerase (Stratagene, La Jolla, Calif.), the 3576 bp of the GALLS coding sequence from pLH441, a derivative of pLH426 (Hodges et al., (2009) J Bacteriol 191: 355-364) that lacks an internal 1734-bp NcoI fragment, was amplified. The 3594-bp amplicon was inserted into the SmaI site of pBluescript KS+ to generate pE3448. After sequencing the insert, the 1734-bp NcoI fragment of GALLS excised from pLH337 (Hodges et al., 2009) into the NcoI site in pE3448 was inserted to form pLH449, which contained the complete GALLS coding sequence flanked by sites for BamHI (upstream) and XhoI (downstream). Insertion of the 5310-bp GALLS coding sequence fromd pLH449 into the BamHI and XhoI sites of pEG202 generated the bait vector pE3462, which was transformed into *Saccharomyces cerevisiae* CTY10-5d (MATα ade2 trp1-901 leu2-3,112 his3-200 gal4 gal80 URA3::lexA-lacZ) containing an integrated GAL1-lacZ gene controlled by the lexA operator. Transformants were screened for growth at 30° C. on drop-out medium SD/-Ura/-His (Yeast Protocols Handbook PT3024-1 (PR973283), Clontech Laboratories, Mountainview, Calif.). DNA from a colony containing the bait plasmid was further transformed with an *Arabidopsis* cDNA library in pGAD424 (Hwang and Gelvin, 2004). The transformation efficiency was estimated according to the colonies growing on drop-out medium SD/-Ura/-His/-Leu. Transformants containing bait, prey, and reporter vectors were selected on drop-out medium SD/-Ura/-His/-Leu/+X-Gal. Colonies that turned blue within one week were tested for GALLS-interacting proteins encoded by cDNAs on the prey vector. Plasmids from each positive yeast colony were individually extracted and transformed into *E. coli* KC8 (hsdR leuB600 trpC9830 pyr::TnS hisB463 lacDX74 strA galU galK). Transformants were selected on M9 medium containing uracil, histidine, tryptophan, and ampicillin but lacking leucine, and the cDNAs were sequenced.

Quantification of Yeast Two Hybrid Interactions:

β-galactosidase activity resulting from interaction between GALLS and LSH10 was quantified using ONPG as described in the Yeast Protocols Handbook (Clontech Laboratories, Inc., USA. PT3024-1, 2009). Ten randomly chosen colonies for each test pair were inoculated in SD/+Gal, grown overnight at 30° C., subcultured the next day, and grown to mid-log phase (A600=0.5-0.8). Cells (1.5 ml) were harvested by centrifugation and washed with 1.5 ml Z buffer (60 mM Na2HPO4, 40 mM NaH2PO4, 10 mM KCl mM MgSO4, pH7.0). Washed cells were resuspended in 0.3 ml Z buffer. An aliquot of 0.1 ml cell suspension was disrupted by three cycles of freezing in liquid N2 and thawing at 37° C. The lysates were diluted with 0.7 ml Z buffer containing 0.27% β-mercaptoethanol followed by addition of 160 ml 4 mg/ml ONPG (Sigma, USA) in Z buffer. The reaction was conducted at 30° C. and terminated by addition of 0.4 ml 1M Na2CO3. The A420 of each reaction was measured after removal of cell debris by centrifugation. β-galactosidase units were calculated as: β-galactosidase units=1,000× A420/(t×V×A600), where: t=incubation time (in min); V=0.1 ml×concentration factor; A600=A600 of the culture.

Vector Construction for Bimolecular Fluorescence Complementation (BiFC) and Subcellular Localization:

For BiFC experiments, the coding regions of the potential interacting proteins were individually fused in-frame with the N- or C-terminal region (nVenus 1-173; cYFP 155-239) of the fluorescent protein Venus (Lee et al., (2008) Plant Methods 4:24). Coding regions were amplified using primers listed in FIG. 12. The fragments were introduced into the expression vector pSAT1-nVenus-N1 (Lee et al., 2008). Plasmids expressing each pair of proteins were introduced into tobacco BY-2 protoplasts by polyethylene glycol-(PEG) mediated transfection (Lee et al., 2008).

Protoplast Preparation, Transfection, and Microscopy:

Tobacco BY-2 protoplasts were prepared and transfected as previously described (Lee et al., (2012) Plant Cell 24: 1746-1759). Fluorescence was imaged using a Nikon Eclipse E600 microscope equipped with YFP-, RFP- (DsRed), and UV-specific filters. To examine the subcellular localization of proteins, the nVenus fragments of the plasmids used for BiFC were replaced with the full-length Venus coding fragment using the enzymes BamHI and NotI. To detect the effect of protein size on nuclear localization, a fragment encoding GUS was inserted between LSH10 and Venus using the restriction enzymes BamHI and EcoRI. The gusA gene was amplified from pCAMBIA-1301 (http://www.cambia.org/daisy/cambia/585.html) using primers listed in FIG. 12. To examine the transfection efficiency of *Arabidopsis* lines, leaf protoplasts were isolated from LSH10-overexpressing lines 3, 35, and 36 and separately transfected, as described (Wu et al., (2009) Plant Meth 5:16), with 7.2 μg of pE3561 (encoding VirD2-Venus). The cells were imaged after 24 h using a Nikon Eclipse E600 epifluorescence microscope.

GST Pull-Down Assay:

To construct Strep-His6-tagged GALLS, we cleaved the expression vector pTrc99 (Amman et al., (1988)) with NcoI and BamHI and inserted annealed oligonucleotides (gallex 3 and gallex 4, FIG. 12) to create pLH378. These oligonucleotides encode methionine and alanine followed by six histidines fused in frame to codons of 3-27 GALLS, including the BglII site at nucleotides 78-83 in the GALLS coding sequence. This placed the 5' end of the 6-His-tagged GALLS coding sequence downstream of the trc promoter. pLH378 was cleaved with KpnI and BamHI and annealed oligonucleotides (gallex 5 and gallex 6, FIG. 12) were inserted to create pLH381. These oligonucleotides include the last eight codons of the GALLS gene, from the SacII site at nucleotides 5286-5291 through the stop codon. pLH381 was cleaved with BglII and a 3,222-bp BglII fragment containing nucleotides 79-3301 from the GALLS coding sequence was inserted to create pLH387. To create pLH388, which expresses 6-His-tagged GALLS protein from the trc promoter, pLH387 was cleaved with EcoRI and SacII and a 3,271-bp EcoRI-SacII fragment containing nucleotides 2018-5289 from the GALLS coding sequence was inserted. pLH388 was cleaved with EcoRI and BamHI and annealed oligonucleotides ESBFwd and ESBRev (FIG. 12) was inserted to create pLH451. pLH451 was cleaved with NcoI and annealed oligonucleotides encoding a streptavidin affinity tag (strep F and strep R, FIG. 12) were inserted to create pLH452. pLH452 was cleaved with EcoRI and BamHI and an EcoRI-BamHI fragment that contains the 6-His-tagged GALLS coding sequence from pLH388, creating pLH458, which expresses Step-6-His-tagged GALLS 1 from the trc promoter was inserted. pLH458 was cleaved with SalI and the entire plasmid was inserted into the SalI site of broad-host-range vector pVK100 (Knauf and Nester, (1982) Plasmid 8: 45-54) to create pLH459. After introduction of pLH459 into *A. tumefaciens* mx358 (virE2::Tn3-lacZ; Stachel and Nester, (1986) EMBO J 5: 1445-1454), His-Strep tagged GALLS-FL was purified by tandem affinity chromatography.

LSH10 was amplified with specific primers (FIG. 12) and inserted into the BamHI and EcoRI sites of pGEXSX-1, fusing the coding regions of LSH10 in-frame with glutathione-S-transferase (GST). GST-LSH10 fusion protein was purified by affinity chromatography using Glutathione S-transferase (GST) Gene Fusion System (GE Healthcare Bio-Sciences Corp., USA) beads in a GST MicroSpin Purification Module according to the manufacturer's protocol. The purified GALLS-FL and GST-LSH10 were incubated together with Glutathione Sepharose 4B in 1×PBS buffer (140 mM NaCl, 2.7 mM KCl, 10 mM Na2HPO4, 1.8 mM KH2PO4, pH 7.3) for 1 hour at room temperature. The mixture was set in a gravity flow column, and the Glutathione Sepharose 4B resin set was washed with five bedresin volumes of 1×PBS buffer. Proteins bound to the resin were eluted with elution buffer. Proteins were fractionated by SDS-PAGE and transferred to membranes. The immunoblots were probed as described with GALLS-specific antibodies (Hodges et al., 2009).

Generation of Transgenic Plants:

To generate *Arabidopsis* overexpression lines, the coding regions of LSH10, with some 5' and 3' untranslated sequences (see FIG. 12), was cloned into the XhoI-SpeI sites of the T-DNA binary vector pE1774 (Lee et al. (2007) Plant Physiol 145: 1294-1300). This binary vector was introduced into *A. tumefaciens* GV3101 by electroporation and used to generate transgenic *Arabidopsis* plants (ecotype Ws) by floral dip (Clough and Bent, (1998) Plant J 16: 735-743). T0 generation seeds were germinated on Gamborg's B5 medium (Caisson Laboratories, Logan, Utah) agar plates containing 100 µg/ml timentin and 10 µg/ml phosphinothricin to select for transgenic plants.

LSH10 mRNA Levels:

RNA was extracted from 3-week-old root of *A. thaliana* plants grown on ½ MS using TRIzol reagent (Invitrogen, USA) according to the manufacturer's instructions. The cDNA was reverse-transcribed using SuperScript® VILO™ cDNA Synthesis Kit (Invitrogen, USA). Specific RT-PCR primers were designed for amplification of LSH10, LSH3, and the control gene ACT2 (At3g18780; FIG. 12). The amplicon lengths were 225 bp for LSH10, 142 bp for LSH3, and 68 bp for ACT2. PCR was performed using the following cycling conditions: 95° C. 2 min for 1 cycle; (95° C. 15 sec, 60° C. 30 sec, 72° C. 30 sec) for 25 cycles. PCR amplicons were separated by agarose gel electrophoresis. LSH10-encoded mRNA levels in roots of transgenic and wild-type *A. thaliana* were also compared by high-throughput sequencing of RNA isolated from roots of wild-type (Ws-2) and transgenic (OE3, OE35, and OE36) plants. For each line, RNA was prepared from three biological replicates that contained roots from 20 plants per sample. Plants were grown in 50 ml of liquid Gamborg's B5 medium shaken at 100 rpm in 250 ml flasks at 25° C. with continuous light. Roots were harvested from 3-week-old plants and frozen in liquid nitrogen. Total RNA (~2 µg) was extracted from ~100 mg of root tissue using the TriZol (Invitrogen) method (Johansen and Carrington, 2001) and further purified using an RNeasy plant mini kit (Qiagen) according to the manufacturer's instructions. Concentration and integrity of RNA was assessed using an Agilent Bioanalyzer 2100. An Illumina TruSeq RNA library preparation kit was used to purify polyA-containing mRNA, convert the mRNA to cDNA, and ligate bar-coded Illumina adapters to the cDNAs. The 12 bar-coded cDNA libraries were sequenced in two Illumina HiSeq 2000 flow cells, providing two technical replicates per sample and generating ~450 million 50-bp single-end reads. Quality of the reads was assessed using the FastQC v 0.10.0 program (http://www.bioinformatics.babraham.ac.uk/projects/fastqc/). Alignment and differential expression analysis was done using the TopHat and Cufflinks programs (Trapnell et al., (2012) Nature Protoc 7: 562-578). Reads were aligned to the *A. thaliana* reference genome using TopHat (http://tophat.cbcb.umd.edu/), and differential expression values were generated using the Cuffdiff program.

Root Transformation Assays:

Root transformation assays were conducted as described (Tenea et al., 2009, ibid). Inoculation concentrations are indicated in the figures. Tumors were scored one month (*A. tumefaciens* A348 and At1811) or six weeks (*A. rhizogenes* R1000) after inoculation. For transient transformation, we used *A. tumefaciens* At849 at the concentrations indicated in the figures. The root segments for transient assays were scored for GUS expression six days after inoculation by staining with X-gluc. For each data point, root segments from 10 plants were pooled, and data from a minimum of five pools were averaged.

Protein Blot Analysis of GIP-Venus Deletion Proteins Transiently Synthesized in Tobacco BY-2 Protoplasts:

Tobacco BY-2 protoplasts were transfected with 10 µg DNA and proteins were extracted 24 hr later. After electrophoresis through 12.5% polyacrylamide gels, the proteins were blotted onto a BioTrace PVDF membrane (PALL Gelman Sciences) and probed with primary antibodies directed against GFP (Anti-GFP, a mixture of two monoclonal antibodies; Roche) and anti-mouse IgG HRP (Promega) as secondary antibody. Blots were developed using a Western Blotting Luminol Reagent (Santa Cruz sc-2048).

*Agrobacterium* Attachment Assays:

Roots from *A. thaliana* plants grown on vertical plates containing B5 medium plus 2% sucrose were cut into ~5 mm segments. The root segments were placed into 2 ml B5 liquid medium in a 6-well microtitre plate and inoculated with *A. tumefaciens* At1961 (strain A348 containing a plasmid encoding GFP) at a final bacterial concentration of 105 cfu/ml. The plates were incubated in the dark without agitation at room temperature for 24 h. The bacterial solution was removed, the roots washed with 5 ml B5 medium for 15 minutes with gentle agitation (50 rpm), the wash solution was removed, and the roots were resuspended in 2 ml B5 medium. GFP-fluorescent bacteria attached to the roots were imaged using a Nikon Eclipse E600 epifluorescence microscope.

Inoculation of *A. thaliana* Plants with *Botrytis cinerea*:

Four-week-old *A. thaliana* plants (ecotype Ws) grown in soil were spray inoculated with spores of *Botrytis cinerea* strain BO5.10 (2.5×105 spores/ml). Photographs were taken seven days after inoculation.

Results:

Identification of a GALLS-Interacting Protein (GIP):

To identify *A. thaliana* proteins that interact with GALLS, a yeast two-hybrid screen was conducted using an *A. thaliana* cDNA library as prey and GALLS-FL as bait. This library was constructed from RNA extracted from whole seedlings of ecotype Col-0 plants (Ballas and Citovsky, (1997) Proc Natl Acad Sci USA 94: 10723-10728). 34 positive colonies were identified from ~106 yeast transformants. All of the cDNAs contained in these colonies encode the same protein, which was termed GIP (GALLS Interacting Protein). The absence of genes encoding other interacting proteins in the cDNA library suggested that the GALLS-GIP interaction is specific. GIP (At2g42610; LSH10) is one of a 10-member gene family whose other described members, LSH1 (LIGHT-DEPENDENT SHORT HYPOCOTYLS 1), LSH3 (OBO1; ORGAN BOUNDARY 1), and LSH4 mediate light regulation of seedling development (Zhao et al., (2004) Plant J 37: 694-706), meristem maintenance (Cho and Zambryski, (2011) Proc Natl Acad Sci USA 108: 2154-2159; Takeda et al., (2011) Plant J 66: 1066-1077), and shoot regeneration (Cary et al., (2002) Plant J 32: 867-877; Motte et al., (2013) Plant Physiol 11: 1229-1241). The LSH10 gene has a 178-codon open reading frame and contains a 1535-bp intron in the 3' untranslated region, which was confirmed by RNA-Seq analysis.

Figure 9:
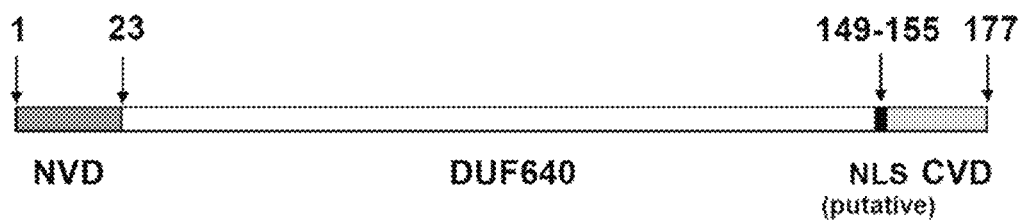
FIG. 9 is a schematic representation of the LSH10 (GIP) protein.

LSH proteins contain a conserved central domain of unknown function (DUF640) flanked by amino- and carboxy-terminal variable domains (NVD, CVD; FIG. 9). LSH proteins also contain putative monopartite SV40-type NLS sequences overlapping the DUF640 and the adjacent CVD (Zhao et al., (2004) Plant J 37: 694-706).

The interaction of LSH10 and GALLS-FL in yeast was quantified. FIG. 1A shows that interaction of GALLS-FL with LSH10 yielded 6 β-galactosidase units, whereas the empty and prey control transformants yielded undetectable activity. While not wishing to be bound by theory, yeast transformed with the prey vector containing LSH10 in the absence of a bait vector produced a small amount (<1 unit) of β-galactosidase (FIG. 1A), suggesting that LSH10 may bind the LexA operator and stimulate transcription of the lacZ reporter gene downstream. Yeast harboring prey vectors containing LSH10 and the empty bait vector pEG202 yielded β-galactosidase levels comparable to those produced in the absence of pEG202 (~1 unit; FIG. 1A).

Figure 1B:
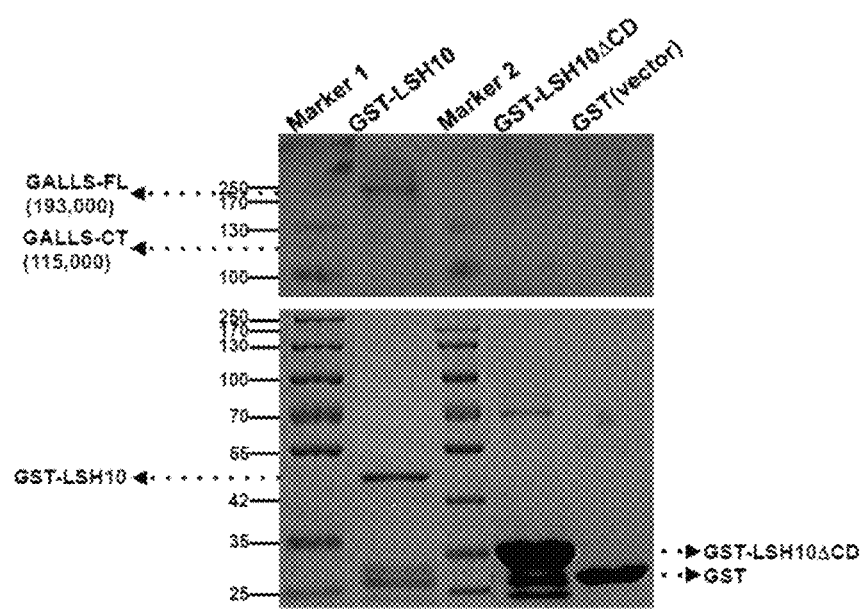
FIG. 1B is a photograph of an SDS-PAGE gel showing the interaction of LSH10 with GALLS-FL in vitro.

To determine whether LSH10 directly interacts with GALLS, recombinant GALLS-FL protein, produced in E. coli, was incubated with glutathione-S-transferase (GST)-tagged LSH10. After purification of complexes by glutathione affinity chromatography, protein blot analysis using anti-GALLS antibody was performed. FIG. 1B (top panel) shows that LSH10 directly interacted with GALLS-FL. Deletion of the central DUF640 domain from LSH10 abrogated these interactions, implicating the central DUF640 domain in GALLS binding activity. FIG. 1B (lower panel) indicates the size and quantity of the GST fusion proteins used in this experiment.

Figure 1C:
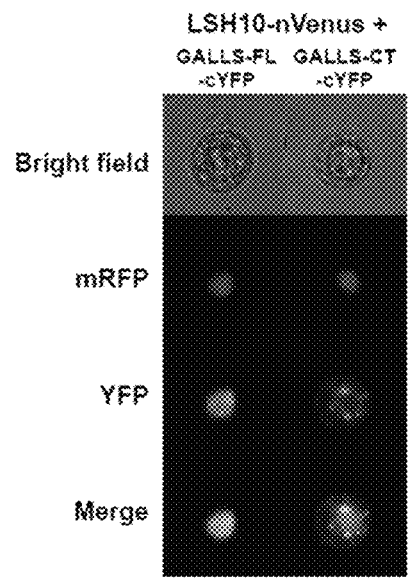
FIG. 1C is an epifluorescence micrograph showing the interaction of LSH10-nVenus with GALLS-FL-cYFP and GALLS-CT-cYFP in tobacco BY-2 protoplasts.

Bimolecular fluorescence complementation (BiFC) was used to test whether LSH10 interacts with GALLS in plant cells (FIG. 1C). LSH10 tagged with the N-terminal fragment of the autofluorescent protein Venus (LSH10-nVenus) interacted with GALLS-FL tagged with the C-terminal fragment of YFP (GALLS-FL-cYFP) predominantly in the nucleus. In contrast, GALLS-CT-cYFP, which lacks the NLS, interacted with LSH10-nVenus in the cytoplasm (FIG. 1C).

Figure 2C:
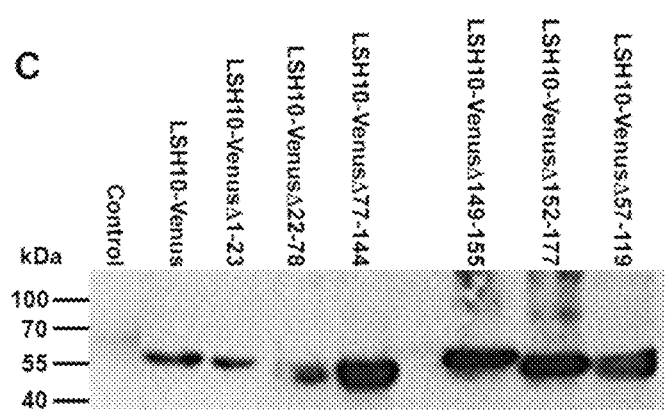
FIG. 2C is photograph of a western blot analysis of LSH10-Venus deletion proteins transiently synthesized in tobacco BY-2 protoplasts.
Figures 2A, 2B:
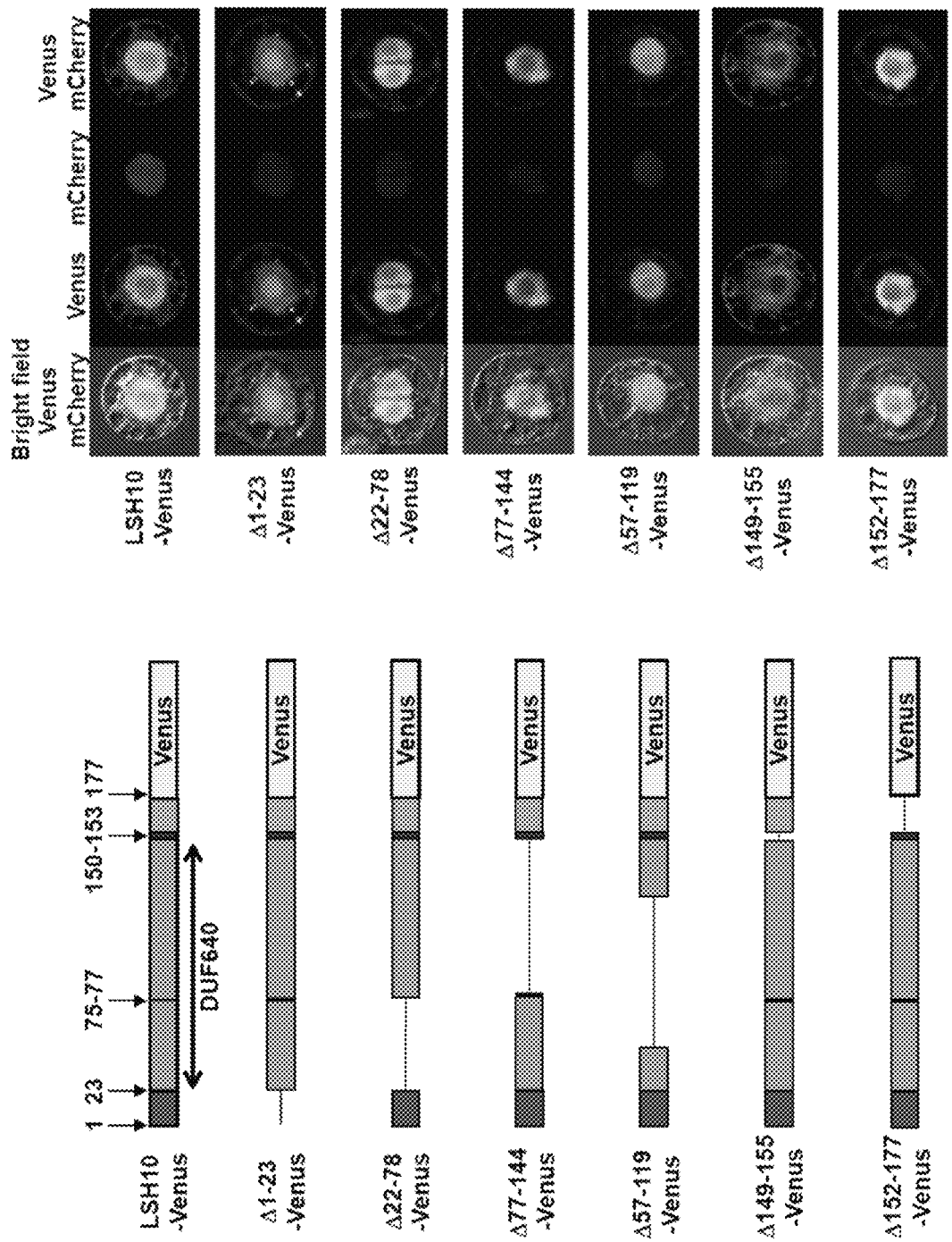
FIG. 2A is schematic diagrams of Venus-tagged deletions of LSH10.
FIG. 2B is a fluorescence micrograph showing the sub-cellular localization of each of the LSH10-Venus deletions.
Figure 3B:
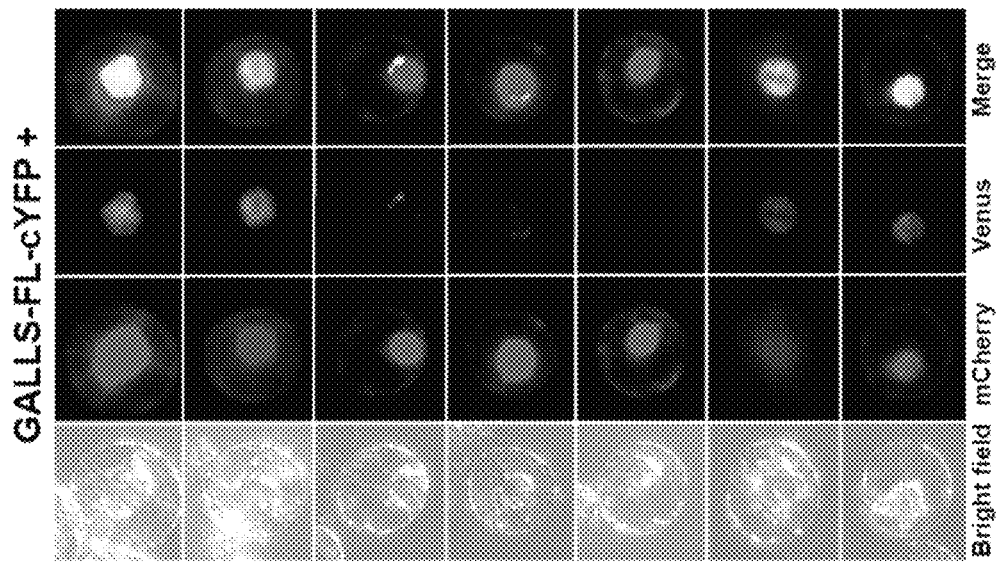
FIG. 3B is an epifluorescence micrograph showing the interaction of GALLS-FL-cYFP with each of the LSH10-nVenus deletions.
Figure 3A:
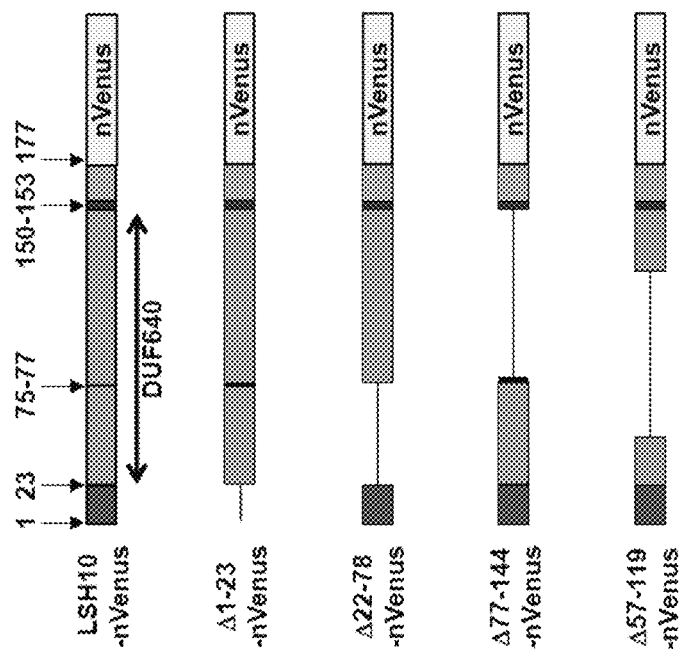
FIG. 3A is schematic diagrams of nVenus-tagged deletions of LSH10.
Figures 10A, 10B:
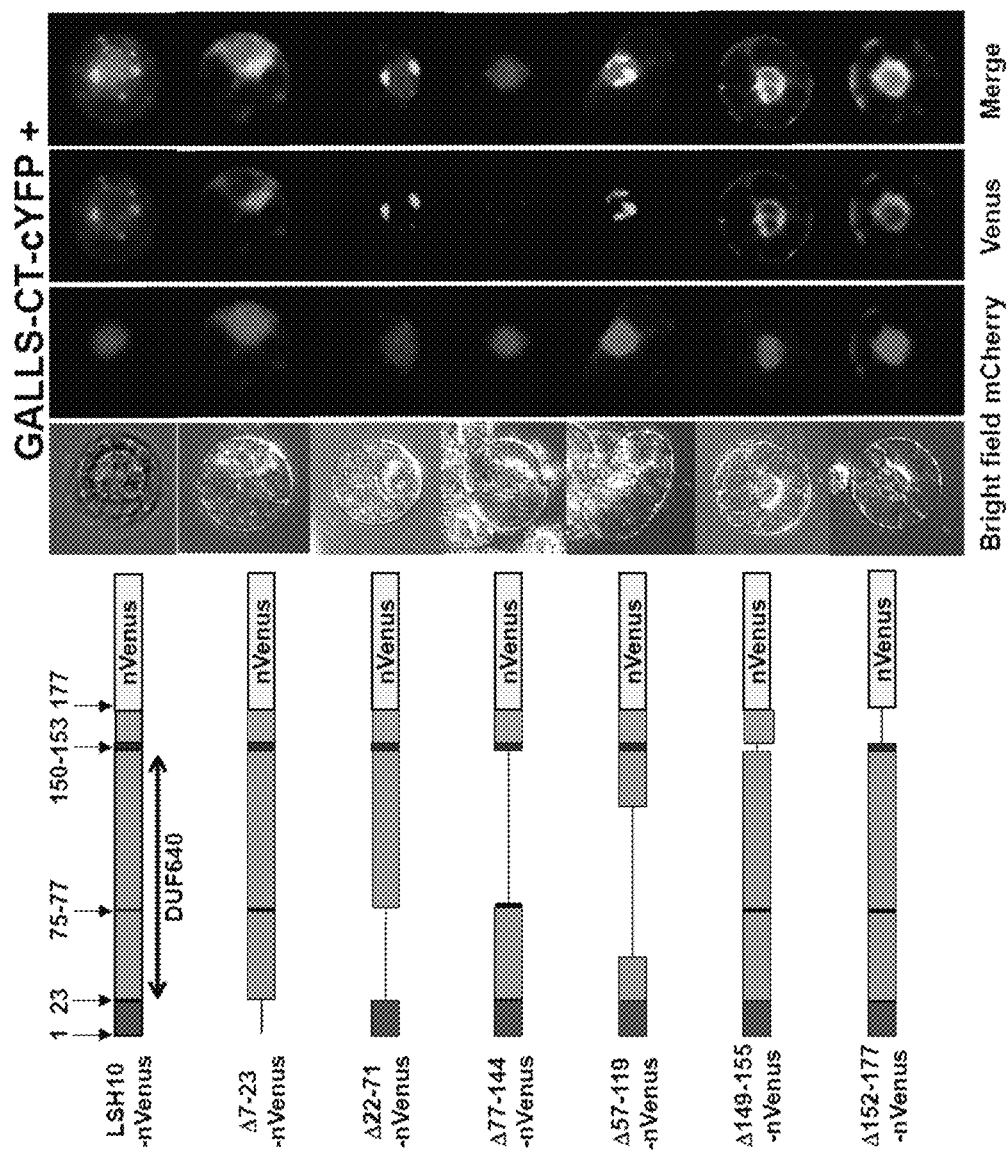
FIG. 10A is schematic diagrams of nVenus-tagged deletions of LSH10.
FIG. 10B is an epifluorescence micrograph showing the interaction of GALLS-FL-cYFP with each of the LSH10-nVenus deletions.

The conserved DUF640 domain of LSH10 was important for interaction with GALLS-FL (FIGS. 3A, B; numbers above the top bar indicate codons at deletion endpoints). Little or no interaction was detected between GALLS-FL-cYFP and nVenus-tagged truncated LSH10 proteins lacking parts of the DUF640 domain. Similarly, the conserved DUF640 domain of LSH10 was important for interaction with GALLS-CT (FIGS. 10A-B). Deletions that removed the putative NLS of LSH10 did not prevent nuclear localization of BiFC complexes with GALLS-FL (FIGS. 3A-B), suggesting that the GALLS-FL NLS may direct the complex to the nucleus. To test the activity of the putative NLS in LSH10, full-length and truncated LSH10-Venus fusion proteins were expressed in tobacco protoplasts. Confocal imaging showed that deletion of the putative NLS (residues 149-155) decreased fluorescence in the nucleus and increased fluorescence in the cytoplasm and perinuclear regions, whereas all other LSH10-Venus fusion proteins localized primarily in the nucleus (FIGS. 2A-C). FIG. 2A shows schematic diagrams of Venus-tagged deletions of LSH10. Numbers above the top bar indicate codons at deletion endpoints. Dark and light blue bars indicate the NVD and CVD, respectively. The orange bar indicates the DUF640 domain, and the red bar indicates the putative NLS. FIG. 2B shows subcellular localization of each of the LSH10-Venus deletions. 10 mg of each construction encoding a LSH10-Venus deletion protein were co-transfected with 10 mg of a Protein blots indicated that all LSH10 deletion constructions produced stable fusion proteins when introduced into tobacco BY-2 cells (FIG. 2C). Protoplasts were transfected with 10 mg DNA and proteins extracted 24 hr later. After electrophoresis through 12.5% polyacrylamide gels, the proteins were blotted onto BioTrace PVDF membrane and probed with antibodies directed against GFP and anti-mouse IgG-HRP as a secondary antibody. Blots were developed using a Western Blotting Luminol Reagent. The control was proteins extracted from non-transfected protoplasts.

Figures 11A, 11B:
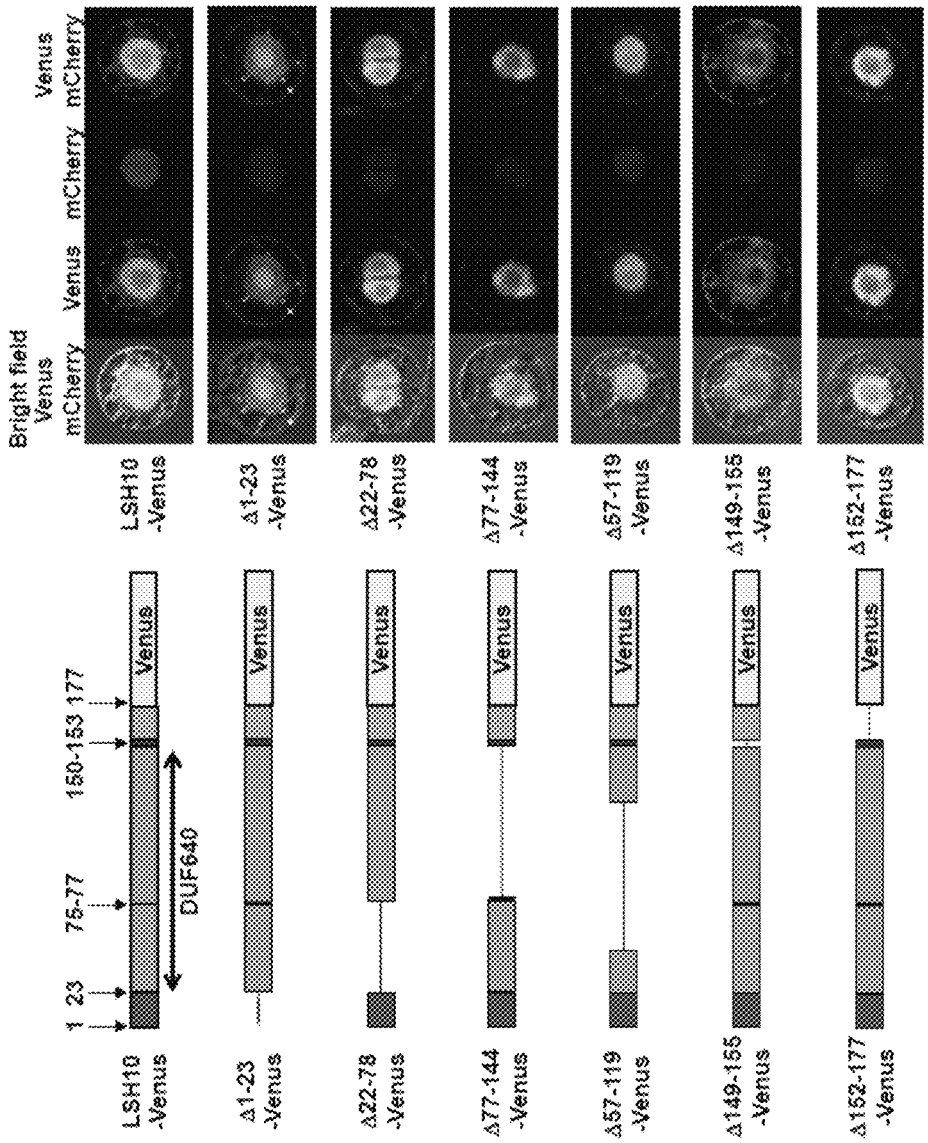
FIG. 11A is schematic diagrams of nVenus-tagged deletions of LSH10.
FIG. 11B is an epifluorescence micrograph showing the interaction of GALLS-FL-cYFP with each of the LSH10-nVenus deletions.

Mutation of LSH10 does not Alter Transformation Susceptibility of A. thaliana Roots:

To determine whether LSH10 is essential for GALLS-dependent Agrobacterium-mediated transformation, tumorigenesis assays (Zhu et al., (2003) Plant Physiol 132: 494-505) were conducted on root segments of the homozygous A. thaliana lsh10 mutant SALK_006965. This mutant line contained a T-DNA insertion in the LSH10 coding region and did not express detectable full-length LSH10 mRNA (FIG. 11A). Root segments of wild-type and lsh10-mutant plants were inoculated with a derivative of A. tumefaciens mx358 (Stachel and Nester, 1986, ibid.). This strain (At1811) contained a Tn3::HoHo1 insertion in virE2 and therefore lacked virE2 and (because of polar effects) virE3 activity. The strain also contained a plasmid expressing GALLS, which restored virulence (Hodges et al., 2004, ibid.). Wild-type and lsh10-mutant plants were equally susceptible to GALLS-dependent Agrobacterium-mediated transformation (FIG. 11B). Other LSH family members expressed in A. thaliana roots may compensate for loss of LSH10. Alternatively, LSH10, while influencing Agrobacterium-mediated transformation of roots (see below), may not be absolutely necessary for transformation.

Overexpression of LSH10 Increases GALLS- and VirE2-Mediated Transformation:

Because functional redundancy among LSH family members may mask participation of LSH10 in Agrobacterium-mediated transformation, a transgenic A. thaliana was created that overexpressed LSH10 to test whether high levels of expression could stimulate GALLS-dependent Agrobacterium-mediated transformation of A. thaliana roots. For these experiments, ecotype Ws was used rather than Col-0, because tumors generated on Ws roots show a wider variety of phenotypes than do tumors on roots of Col-0 plants (Zhu et al., 2003, ibid.). Thus, it was easier to compare tumorigenesis on roots of LSH10 overexpressing and wild-type plants. High-throughput sequencing of RNA isolated from roots of three LSH10-transgenic A. thaliana lines (OE3, OE35, and OE36) revealed that these lines contained 46- to 90-fold more LSH10-encoded RNA than did roots from the parental Ws ecotype (Table 1).

TABLE 1

Expression of LSH genes in wild-type and transgenic A. thliana roots.

| Gene | Ws2 | OE3 | OE35 | OE36 |
|---|---|---|---|---|
| LSH1 | 0.07 | 1.36 | 0.23 | 0.98 |
| LSH2 | 0.05 | 0.60 | 0.25 | 0.67 |
| LSH3 | 5.79 | 4.27 | 4.03 | 5.47 |
| LSH4 | 1.32 | 7.81 | 7.44 | 5.87 |
| LSH5 | 24.99 | 16.18 | 15.12 | 11.00 |
| LSH6 | 29.69 | 36.51 | 20.14 | 24.71 |
| LSH7 | 8.16 | 9.29 | 12.79 | 9.64 |
| LSH8 | 0 | 0 | 0 | 0 |
| LSH9 | 41.81 | 54.03 | 29.81 | 33.47 |
| LSH10 (GIP) | 29.00 | 1345.77 | 2261.29 | 2620.23 |

LSH-encoded mRNA abundance in wild-type (Ws2) and LSH10-transgenic (OE3, OE35, and OE36) A. thaliana roots. Numbers indicate fragments per kilobase of transcript per million mapped reads (FPKM).

Expression of LSH10 from the strong superpromoter (Lee et al., (2007) Plant Physiol 145: 1294-1300) in transgenic A.

Figure 4A:
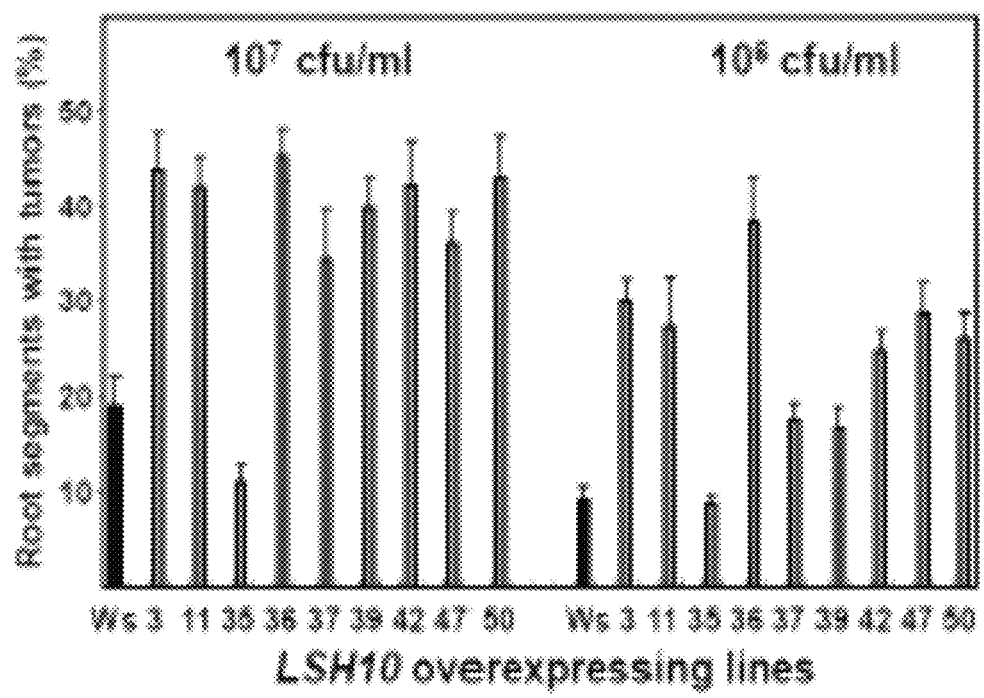
FIG. 4A is a graph showing the effect of LSH10 overexpression on susceptibility to stable *A. tumefaciens* At1811 GALLS-mediated transformation.
Figure 4B:
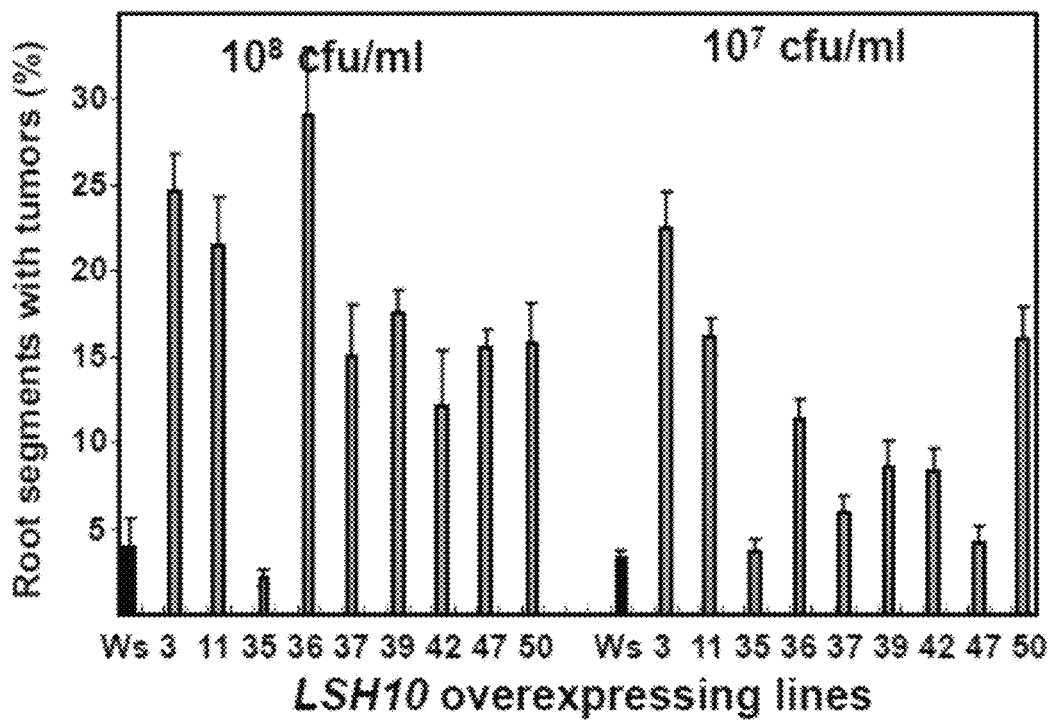
FIG. 4B is a graph showing the effect of LSH10 overexpression on susceptibility to stable *A. rhizogenes* R1000 GALLS-mediated transformation.
Figure 4C:
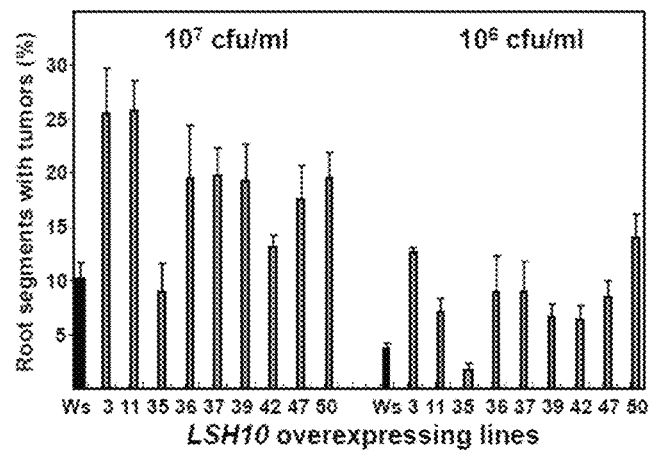
FIG. 4C is a graph showing the effect of LSH10 overexpression on susceptibility to stable *A. tumefaciens* A348 VirE2-mediated transformation.

*thaliana* increased susceptibility of roots to *Agrobacterium*-mediated transformation. Of nine T2 generation transgenic lines overexpressing LSH10, eight showed 2- to 4-fold greater sensitivity to GALLS-mediated transformation than did the parental Ws genotype (FIG. 4A). Root segments of these LSH10-overexpressing lines were up to 7-fold more susceptible than were Ws plants to transformation by *A. rhizogenes* R1000 (FIG. 4B). These same lines also displayed increased susceptibility to VirE2-mediated transformation (FIG. 4C). These results indicate that increased levels of LSH10 stimulate transformation by *A. tumefaciens* and *A. rhizogenes*.

Figure 4D:
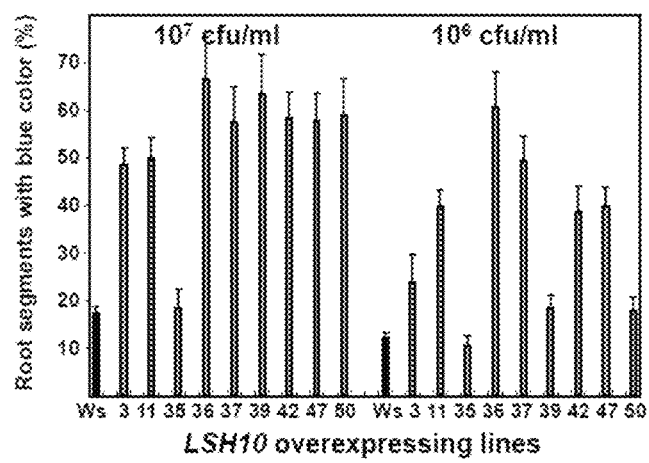
FIG. 4D is a graph showing the effect of LSH10 overexpression on susceptibility to transient *A. tumefaciens* At1849-mediated transformation.

LSH10 Contributes to Early Stages of Transformation:

*Agrobacterium*-mediated plant transformation consists of numerous steps, including bacterial attachment to the plant, T-DNA and virulence protein transfer, cytoplasmic trafficking and nuclear targeting of T-DNA-protein complexes, and T-DNA integration. Stable transformation involves all these steps; the tumorigenesis assays reflect this process. However, transient transformation involves T-DNA and virulence protein transfer and T-DNA expression prior to T-DNA integration into the genome (Gelvin, (2010b) Annu Rev Phytopathol 48: 45-68). Transgenic *A. thaliana* lines that overexpress LSH10 were tested for susceptibility to transient transformation by inoculating root segments of these plants with the disarmed (i.e., lacking oncogenes) strain *A. tumefaciens* At849 containing the T-DNA binary vector pBISN1 (Narasimhulu et al., (1996) Plant Cell 8: 873-886). Early β-glucuronidase (GUS) expression directed by the gusA-intron gene of pBISN1 indicated transient transformation (Zhu et al., 2003, ibid.). FIG. 4D shows that the LSH10 overexpressing lines that were hypersusceptible to stable transformation were also hypersusceptible to transient transformation. Thus, LSH10 participates in an early step of plant transformation.

Tests were performed to determine whether overexpression of LSH10 increases susceptibility of transgenic *A. thaliana* to other methods of transformation, such as polyethylene glycol (PEG)-mediated transfection with plasmid DNA. Leaf protoplasts from three LSH10-transgenic *A. thaliana* lines showed similar PEG-mediated transformation frequencies, regardless of their susceptibility to *Agrobacterium*-mediated transformation (Table 2). Thus, overexpression of LSH10 increased susceptibility to *Agrobacterium*-mediated transformation but not PEG-mediated transfection. LSH10 therefore affects aspects of transformation specific to *Agrobacterium*, such as plant defense or intracellular trafficking of virulence protein-DNA complexes, and not processes common to transformation and transfection, such as transgene expression.

TABLE 2

PEG-mediated transfection of leaf protoplasts with a plant-active Venus gene[a].

| LSH10 overexpressing line | Number of cells observed | Number of fluorescent cells | Transfection efficiency |
| --- | --- | --- | --- |
| #3[b] | 997 | 201 | 20.2% |
| #36[b] | 970 | 90 | 9.3% |
| #35[c] | 1017 | 171 | 16.8% |

[a]Protoplasts were transfected with 7.2 μg 6 DNA and fluorescence was observed after 24 h
[b]LSH10 overexpressing line that is hypersusceptible to *Agrobacterium*-mediated transformation
[c]LSH10 overexpressing line not hypersusceptible to *Agrobacterium*-mediated transformation LSH10 Overexpressing Plants do not Show Increased *Agrobacterium* Attachment:

The ability of *Agrobacterium* cells to bind plant cells affects transformation efficiency (Douglas et al., (1982) J Bacteriol 152: 1265-1275); therefore, tests were performed to determine whether LSH10-overexpressing plants bind *Agrobacterium* cells to a greater extent than do roots of wild-type plants. Tumorigenic *A. tumefaciens* A348 containing a plasmid constitutively expressing GFP was incubated with root segments from LSH10-overexpressing plant lines that showed increased (OE3 and OE36) or wild-type (OE35) susceptibility to *Agrobacterium*-mediated transformation. As a control, root segments from wild-type Ws-2 plants were also cocultered. After 24 h, the root segments were washed in B5 medium and observed GFP fluorescence using an epifluorescence microscope. The results show that the root segments from all of these lines bound *Agrobacterium* to approximately the same extent. Thus, increased bacterial attachment to cut root segments cannot account for the observed transformation hypersusceptibility.

LSH10 Interacts with Other *A. tumefaciens* and Plant Proteins Important for Transformation:

*A. tumefaciens* transfers several virulence effector proteins to plant cells where they may form complexes (T-complexes) with T-strands and plant proteins (Howard and Citovsky, (1990) BioEssays 12: 103-108; Gelvin, (2010a) Curr Opin Microbiol 13: 53-58, (2010b), ibid.). VirE2 binds ssDNA and VIP1, a host protein that may form a bridge between VirE2 and importin α proteins to target T-strands to the nucleus (Tzfira et al., (2001) EMBO J 20: 3596-3607; Djamei et al., (2007) Science 318: 453-456; Pitzschke and Hirt, (2010) EMBO J 29: 1021-1032). Plant importin α (IMPa) proteins are involved in nuclear transport of VirE2 and VirD2 (Ballas and Citovsky, 1997, ibid.; Bhattacharjee et al., (2008) Plant Cell 20: 2661-2680; Lee et al., 2008, ibid.), which is covalently attached to the 5' ends of T-strands (Herrera-Estrella et al., (1988) EMBO J 7: 4055-4062; Ward and Barnes, (1988) Science 242: 927-930; Young and Nester, (1988) J Bacteriol 170: 3367-3374). Interactions of LSH10 with these putative T-complex proteins was tested in tobacco BY-2 cells using bimolecular fluorescence complementation.

Figure 5:
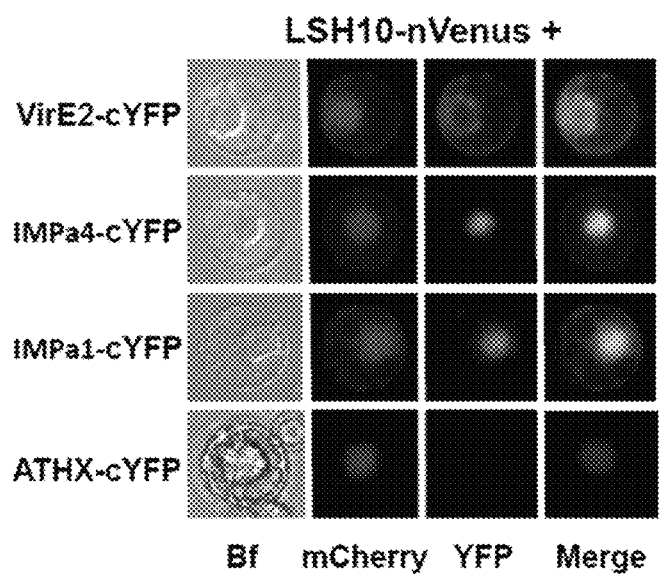
FIG. 5 is an epifluorescence micrograph showing LSH10 interaction with *A. tumefaciens* and plant proteins involved in transformation.

FIG. 5 shows that LSH10 interacted with IMPa-1 and IMPa-4 in the nucleus. LSH10 interacted with VirE2 in the cytoplasm, forming perinuclear rings. To test specificity of LSH10 interactions with plant proteins, BiFC experiments were conducted with LSH10-nVenus and ATHX enzyme activator-cYFP. ATHX enzyme activator (At1g50320) is an *Arabidopsis* protein that interacts with VirE2 (Lee et al., (2012) Plant Cell 24: 1746-1759). FIG. 5 shows that ATHX enzyme activator did not interact with LSH10 (although it did interact with VirE2), indicating specificity of LSH10 interaction with importin-α proteins and VirE2.

Figure 6A:
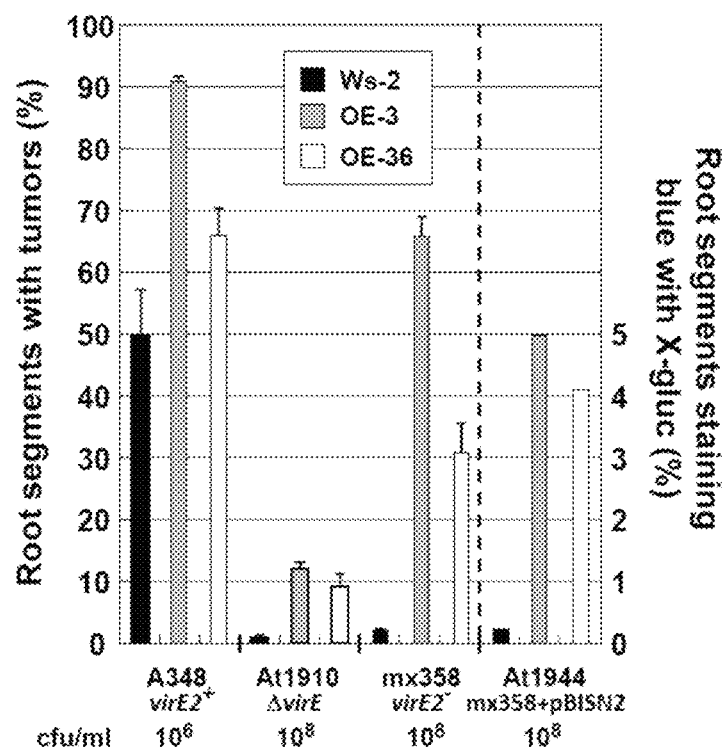
FIG. 6A is a graph illustrating that overexpression of LSH10 results in plants that are susceptible to virE2- and GALLS-independent transformation.
Figure 6B:
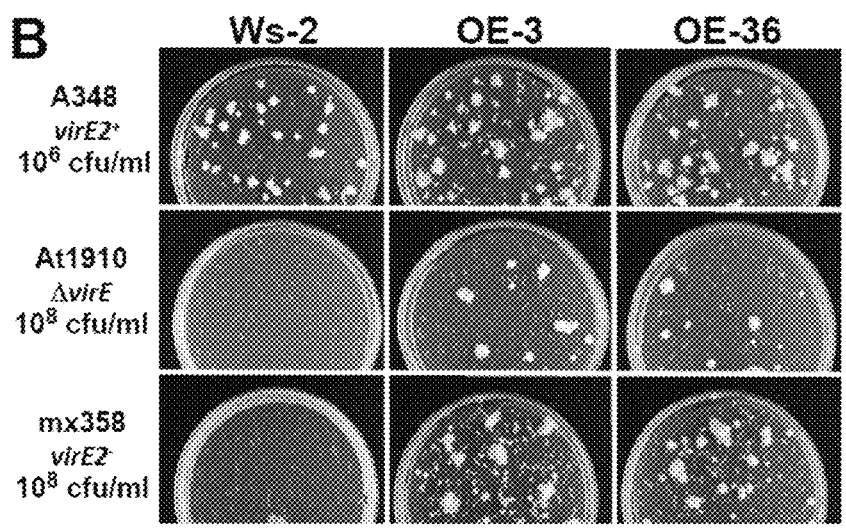
FIG. 6B is a photograph of representative plates showing tumor formation after infection by the indicated *A. tumefaciens* strains.
Figure 6C:
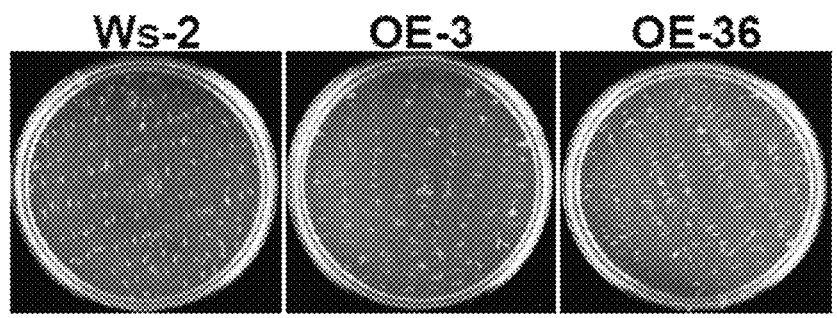
FIG. 6C is a photograph of representative plates showing the lack of calli formation in uninoculated root segments from Ws-2 and LSH10-overexpressing lines 3 and 36.

Overexpression of LSH10 Increases Plant Susceptibility to VirE2- and GALLS-Independent Transformation:

*A. tumefaciens* strains lacking virE2 are highly attenuated in virulence (Stachel and Nester, 1986, ibid.). Tests were performed to determine whether transgenic plants that overexpress LSH10 would show increased transformation susceptibility to *Agrobacterium* strains lacking both virE2 and GALLS. Two LSH10-overexpressing lines (OE3 and OE36) showed increased susceptibility to stable transformation by wild-type *A. tumefaciens* A348 (containing virE2), *A. tumefaciens* At1910 (lacking the virE operon), and virE2-mutant *A. tumefaciens* mx358 (FIGS. 6A and 6B). These LSH10-overexpressing lines also showed increased transient transformation by virE2-mutant *A. tumefaciens* At1944 containing a gusA-intron gene in the T-DNA, verifying increased transformation using an assay that did not rely on phytohormone responses by the plant. Non-inoculated root segments from LSH10-overexpressing lines 3 and 36 did not develop tumors on medium lacking phytohormones, indicating that tumor formation on these roots depended upon transformation by tumorigenic *Agrobacterium* strains (FIG. 6C). Thus, overexpression of LSH10 in transgenic *A. thaliana* roots increased transformation susceptibility to virE2- and GALLS-independent transformation (FIGS. 6A-C) and to GALLS- and virE2-dependent transformation (FIG. 4A-D). While not wishing to be bound by theory, these data suggest that LSH10 stimulates transformation at a step independent of the functions of VirE2 and GALLS.

Overexpression of LSH10 Affects Expression of Defense-Related Genes in Transgenic *A. thaliana*:

LSH10 overexpression stimulated *Agrobacterium*-mediated transformation in most, but not all, transgenic *A. thaliana* lines. Several LSH genes appear to encode transcription factors (Zhao et al., 2004, ibid.; Yoshida et al., (2009) Proc Natl Acad Sci USA 106: 20103-20108; Cho and Zambryski, (2011) Proc Natl Acad Sci USA 108: 2154-2159; Takeda et al., 2011, ibid.), suggesting that LSH10 may regulate host genes that affect susceptibility to *Agrobacterium*-mediated transformation. To identify LSH10-regulated genes that may affect susceptibility to transformation, the transcriptome of the parental ecotype (Ws-2) was compared with the transcriptomes of LSH10-overexpressing lines with increased (OE3 and OE36) or wild-type (OE35) susceptibility to transformation.

RNA-Seq transcriptome analysis of mRNA isolated from roots of plants grown in liquid B5 medium confirmed that all three transgenic lines contained significantly more LSH10-encoded mRNA than did the parental Ws-2 line (Table 1), and the transgenes expressed wild-type mRNA as full-length transcripts that were properly spliced. Roots from line OE35, which showed wild-type susceptibility to transformation, contained more LSH10-encoded mRNA than did one hypersusceptible line (OE3) and less than another hypersusceptible line (OE36) (Table 1). Thus, LSH10 mRNA levels alone cannot explain the failure of LSH10 overexpression to stimulate transformation in line OE35. DNA blot analysis indicated that LSH10-overexpressing lines 3 and 36 each contain two T-DNA insertions, whereas line 35 contains multiple complex T-DNA insertions.

Most LSH genes were expressed in roots of wild-type and transgenic *A. thaliana*. Wild-type roots contained significant levels of mRNA encoded by six LSH genes (LSH3, LSH5, LSH6, LSH7, LSH9, and LSH10), whereas LSH1 and LSH2 encoded very low levels of mRNA and LSH8 mRNA was undetectable (Table 1). In the LSH10-transgenic lines, mRNA levels for LSH1, LSH2, LSH4, and LSH10 increased, whereas the rest of the LSH genes were expressed at wild-type levels (Table 1). Genes that increase transformation susceptibility in LSH10-overexpressing transgenic *A. thaliana* should be differentially expressed in hypersusceptible lines (OE3 and OE36) compared to lines showing wild-type susceptibility to transformation (Ws-2 and OE35). Transcriptome analysis revealed 237 *A. thaliana* genes that fit this profile. Expression of these genes was similar in OE3 and OE36 but differed significantly in Ws-2 and OE35. Within this set, 27 genes also showed significant differences in expression between Ws-2 and OE35. While not wishing to be bound by theory, it may be that one or more of these genes may account for the inability of LSH10 overexpression to stimulate *Agrobacterium*-mediated transformation in line OE35, as it does in other transgenic lines derived from Ws-2. Two such genes, WRKY38 (At5G22570) and WRKY62 (At5G01900), encode type III WRKY transcription factors that repress plant defense responses upon pathogen infection (Kim et al., (2008) Plant Cell 20: 2357-2371). Expression of WRKY38 increased 7- to 13-fold in the hypersusceptible lines (OE36 and OE3) compared to Ws-2, whereas expression decreased 35-fold in line OE35 compared to Ws-2. Similarly, expression of WRKY62 increased 5-fold in the hypersusceptible lines compared to Ws-2, whereas expression decreased 6-fold in line OE35 compared to Ws-2.

Figure 7A:
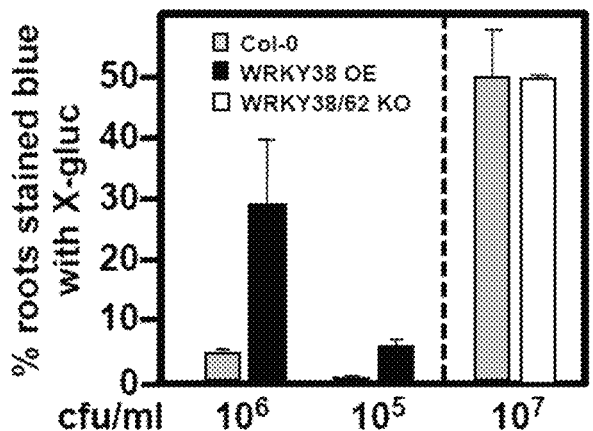
FIG. 7A is a graph showing the effect of WRKY38 on susceptibility to transient transformation by *A. tumefaciens* At849.
Figure 7B:
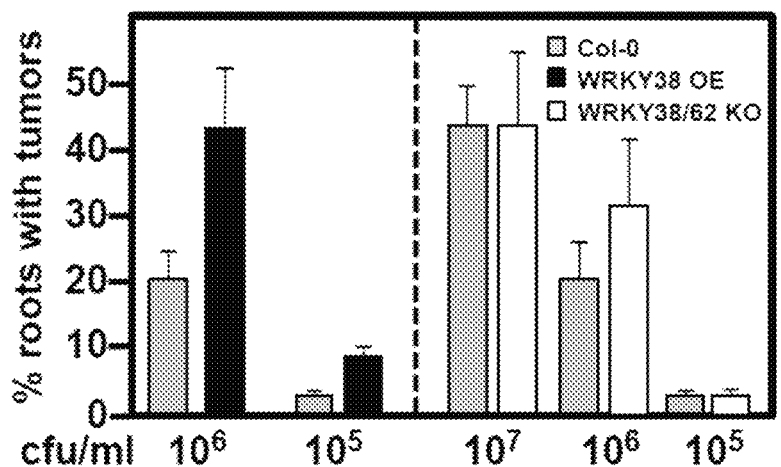
FIG. 7B is a graph showing the effect of WRKY38 on susceptibility to stable transformation by *A. tumefaciens* A208.

Increased expression of transcription factors that suppress the host defense response to bacterial pathogen infection might increase *Agrobacterium*-mediated transformation. To test this possibility, the transformation susceptibility of a transgenic *A. thaliana* line that overproduces WRKY38 (Kim et al., 2008, ibid.) was tested. In this line, transient transformation increased ~six-fold and stable transformation by *A. tumefaciens* increased more than two-fold (FIGS. 7A-B; *A. tumefaciens* concentration along the x-axis), suggesting that overexpression of LSH10 likely stimulates transformation by increasing expression of transcription factors that diminish the host response to bacterial infection. A WRKY38/62 double mutant did not show a significant difference in transient or stable transformation compared to wild-type plants (FIGS. 7A-B), suggesting that other *Arabidopsis* proteins may be functionally redundant with these transcription factors (Eulgem and Somssich, (2007) Cuff Opin Plant Biol 10: 366-371).

Figure 8:
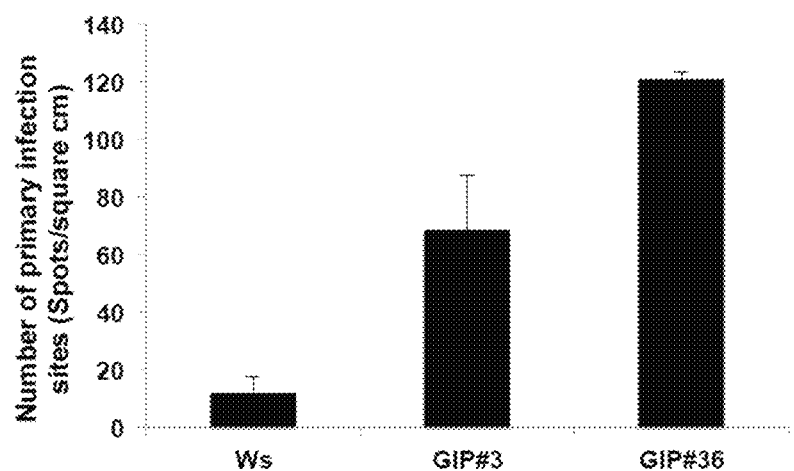
FIG. 8 is a graph showing the susceptibility of LSH10-overexpressing lines 3 and 36 to *Botrytis cynerea*.

LSH10-Overexpressing Lines 3 and 36 Show Increased Susceptibility to *Botrytis cinerea*:

WRKY transcription factors regulate host defense responses to multiple pathogens (Eulgem and Somssich, 2007, ibid.; Rushton et al., (2010) Trends Plant Sci 15: 247-258). For example, increased expression of WRKY38 and WRKY62 in transgenic *A. thaliana* increases susceptibility to infection by *Pseudomonas syringae* (Kim et al., 2008, ibid.). Similarly, overexpression of WRKY38 in transgenic *A. thaliana* increased susceptibility to *Agrobacterium*-mediated transformation (FIG. 7). Because LSH10-overexpressing lines 3 and 36 show increased expression of WRKY38 and WRKY62, tests were performed to determine whether these lines show increased susceptibility to infection by the fungal pathogen *Botrytis cinerea*. Leaves of control Ws-2 and LSH10-overexpressing lines 3 and 36 were inoculated with conidia of *Botrytis cinerea* BO5.10. Seven days after inoculation, these LSH10-overexpressing plants showed increased susceptibility to *B. cinerea* infection (FIG. 8). Thus, these transgenic plants, which overexpress LSH10, WRKY38, and WRKY62, are hypersusceptible to biotrophic and necrotrophic pathogens.

What is claimed is:

1. A transgenic plant or part thereof transformed with a polynucleotide sequence encoding SEQ ID NO: 38, operably linked to a heterologous promoter functional in the plant or part thereof, wherein the plant or part thereof exhibits increased transformability by *Agrobacterium*-mediated transformation relative to a plant or part thereof lacking the polynucleotide sequence.

2. A cell of the transgenic plant of claim 1.

3. A seed of the transgenic plant of claim 1, wherein the seed comprises the polynucleotide sequence encoding SEQ ID NO: 38.

4. The transgenic plant of claim 1, wherein the transgenic plant is a dicot.

5. The transgenic plant of claim 1, wherein the transgenic plant is a monocot.

6. The transgenic plant of claim 1, wherein SEQ ID NO: 38 is overexpressed at a level from about 2 to about 10 times above a basal level.

7. The transgenic plant of claim 1, wherein the *Agrobacterium*-mediated transformation comprises an *Agrobacterium* strain lacking GALLS and VirE2.

8. A method of preparing a transgenic plant or part thereof that is highly efficient in a *Agrobacterium*-mediated transformation, the method comprising
   a. Transforming a polynucleotide sequence operably linked to a heterologous promoter functional in the plant or part thereof, wherein the polynucleotide sequence encodes SEQ ID NO: 38;
   b. Overexpressing SEQ ID NO: 38, at a level of from about 2 to about 10 times above a basal level; and
   c. Exposing the plant or part thereof to Agrobacteria carrying a selected DNA of interest.

* * * * *